US007994120B2

(12) United States Patent
Dasseux et al.

(10) Patent No.: US 7,994,120 B2
(45) Date of Patent: Aug. 9, 2011

(54) METHOD OF TREATING DYSLIPIDEMIC DISORDER

(75) Inventors: Jean-Louis Dasseux, Brighton, MI (US); Thomas J. Rea, Pinckney, MI (US); Anna S. Shenderova, Ann Arbor, MI (US)

(73) Assignee: Pfizer, Inc., Groton, CT (US)

(*) Notice: Subject to any disclaimer, the term of this patent is extended or adjusted under 35 U.S.C. 154(b) by 682 days.

(21) Appl. No.: 11/843,223

(22) Filed: Aug. 22, 2007

(65) Prior Publication Data

US 2008/0269111 A1  Oct. 30, 2008

Related U.S. Application Data

(62) Division of application No. 10/440,213, filed on May 16, 2003, now abandoned.

(60) Provisional application No. 60/381,512, filed on May 17, 2002.

(51) Int. Cl.
*A61K 38/16* (2006.01)
*A61P 3/06* (2006.01)

(52) U.S. Cl. .................. 514/7; 514/2; 514/12; 530/350; 424/9.1

(58) Field of Classification Search .................. 514/2, 7, 514/12; 530/350; 424/9.1
See application file for complete search history.

(56) References Cited

U.S. PATENT DOCUMENTS

| 6,004,925 | A | 12/1999 | Dasseux et al. |
| 6,037,323 | A | 3/2000 | Dasseux et al. |
| 6,046,166 | A | 4/2000 | Dasseux et al. |
| 6,258,596 | B1 | 7/2001 | Benoit et al. |
| 6,265,377 | B1 | 7/2001 | Dasseux et al. |
| 6,329,341 | B1 | 12/2001 | Dasseux et al. |
| 6,376,464 | B1 | 4/2002 | Dasseux et al. |
| 7,435,717 | B2 * | 10/2008 | Bisgaier et al. ................ 514/1.1 |

FOREIGN PATENT DOCUMENTS

| JP | 59-278140 | 12/1984 |
| JP | 61152632 | 7/1986 |
| WO | WO 93/12143 | 6/1993 |
| WO | WO 93/25581 | 12/1993 |
| WO | WO 94/13819 | 6/1994 |
| WO | WO 96/04916 | 2/1996 |
| WO | WO 96/05227 | 2/1996 |
| WO | WO 96/37608 | 11/1996 |
| WO | WO 97/36927 | 10/1997 |
| WO | WO 97/43311 | 11/1997 |
| WO | 9916459 | 4/1999 |
| WO | 0158492 | 8/2001 |
| WO | WO 02/30359 A2 | 4/2002 |
| WO | PCT/US03/015469 | 9/2003 |

OTHER PUBLICATIONS

Ameli, S., et al., "Recombinant Apolipoprotein A-I Milano Reduces Intimal Thickening After Balloon Injury In Hypercholesterolemic Rabbits," (1994), *Circulation*, 90(4), pp. 1935-1941.
Aviram, M., et el., "Paraoxonase Active Site Required for Protection Against LDL Oxidation Involves Its Free Sulfhydryl Group And Is Different From That Required For Its Arylesterase/Paraoxonase Activities: Selective Action Of Human Paraoxonase Allozymes Q And R," (1998), *Arterioscler. Thromb. Vasc. Biol.*, 18, pp. 1617-1624.
Aviram. M., et al, "Paramonase Inhibits High-Density Lipoprotein Oxidation and Preserves Its Functions: A Possible Peroxidative Role For Paraoxonase," (1998), *J. Clin. Invest.*, 101, pp. 1581-1590.
Badimon, I.J., et al., "Regression of Atherosclerotic Lesions by High Density Lipoprotein Plasma Fraction in the Cholesterol-fed Rabbit," (1990), *J. Clin. Invest.*, 85, pp. 1234-1241.
Beitz, J., et al, "Does a HDL Injection Reduce the Development of Serum Hyperlipidemia and Progression of Fatty Streaks in Cholesterol Fed Rabbits?" (1992), *Prostoglandins Leukotrienes and Essential Fatty Acids*, 47, pp. 149-152.
Berard, A.M., et al., "High Plasma HDL Concentrations Associated with Enhanced Atherosclerosis in Transgenic Mice Overexpressing Lecithin-Cholesteryl Acyltransferase," (1997). *Nat. Med.*, 3(7), pp. 744-749.
Billecke, S., et et, "Human Serum Paraoxonase (PON1) Isozymes Q And R Hydrolyze Lactones And Cyclic Carbonate Esters," (2000) *Drug Metab. Dispos.*, 28, pp. 1335-1342.
Carlson, L.A., "Effect of a Single Infusion of Recombinant Human Proapolipoprotein A-I Liposomes (Synthetic HDL) on Plasma Lipoproteins in Patients with Low High Density Lipoprotein Cholesterol," (1995) *Nutr. Metab. Cardiovas. Dis.*, 5, pp. 85-91.
Cheung, M.C., et al, "Altered Particle Size Distribution of Apolipoprotein A-I-Containing Lipoproteins in Subjects with Coronary Artery Disease,"(1991), *J. Lipid Res.*, 32, pp. 383-394.
Corijn, J., et al., "Synthetic Model Peptides for Apolipoproteins. II. Characterization of the Discoidal Complexes Generated Between Phospholipids and Synthetic model Peptides for Apolipoproteins," (1993). *Biochim. Biophys. Acta*, 1170, pp. 8-16.
Dragonov, D.I., et al., "Rabbit Scrum Paraoxonase 3 (PON3) is A High Density Lipoprotein-Associated Lactonase and Protects Low Density Lipoprotein Against Oxidation," (2000), *J. Biol. Chem.*, 275 (43), 33435-33442.
Duverger, N., et al., "Inhibition of Atherosclerosis Development in Cholesterol-Fed Human Apolipoprotein A-1-Transgenic Rabbits," (1996), *Circulation*, 994(4), pp. 713-717.
Dyer, C.A.,et al., "Only Multimers Of A Synthetic Peptide Of Human Apolipoprotein E Are Biologically Active," (1991), *J. Biol. Chem.*, 266(23), pp. 15009-15015.
Dyer, C.A., et al., "Structural Features of Synthetic Peptides of Apolipoprotein E Bind the LDI Receptor," (1995), *J. Lipid. Res.*, 36, pp. 80-88.
Emmanuel, F.,et al. "Identification of Specific Amphipathic α-Helical Sequence of Human Apolipoprotein A-IV Involved In Lecithin: Cholesterol Acyltransferase Activation," (1994), *J. Biol. Chem.*, 269(47), pp. 29883-29890.

(Continued)

*Primary Examiner* — Chih-Min Kam
(74) *Attorney, Agent, or Firm* — Roylance, Abrams, Berdo & Goodman, LLP

(57) ABSTRACT

The invention provides methods of treating or preventing a condition or disorder associated with dyslipidemia with compositions comprising apolipoprotein-sphingomyelin complexes. The methods of the invention permit reduction, by 4- to 20-fold, of the amount of apolipoprotein required for therapeutic administration to bring about an ameliorative effect.

1 Claim, 1 Drawing Sheet

OTHER PUBLICATIONS

Figure 1:
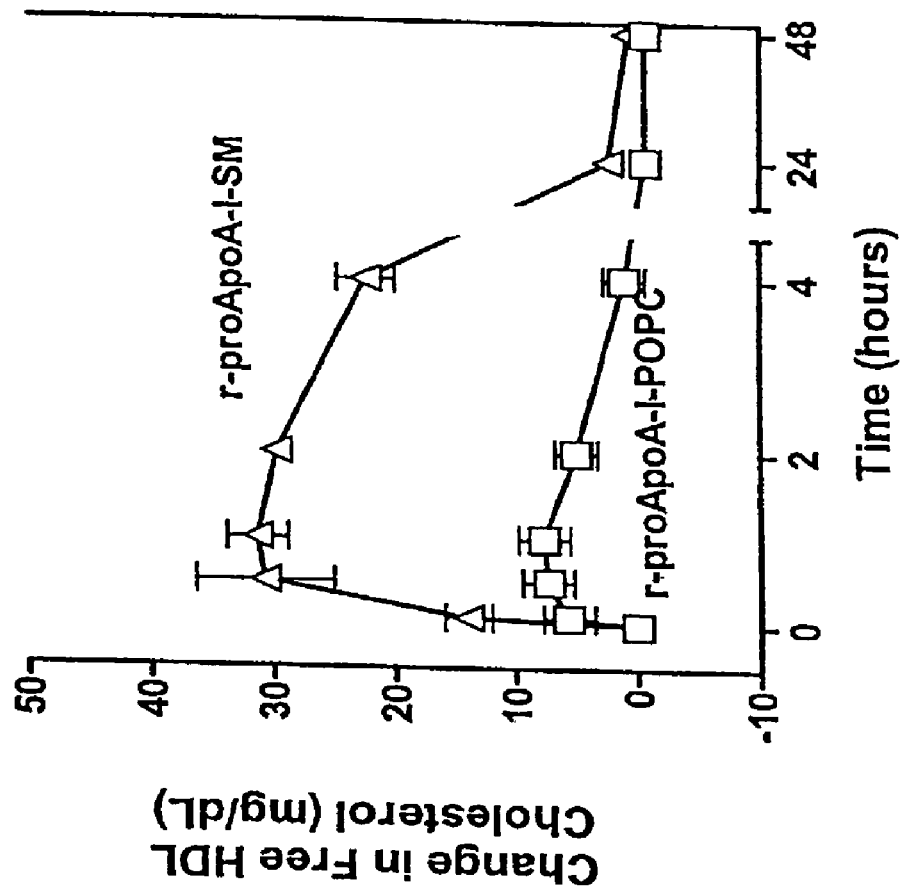

Fournier, N., et al., "Role of HDL Phospholipid in Efflux of Cell Cholesterol to Whole Serum: Studies with Human apoA-1 Transgenic Rats," (1996) *J. Lipid Res.*, 37, pp. 1704-1711.

Franceschini, G., et al., "A-I$_{MILANO}$Apoprotein: Decreased High Density Lipoprotein Cholesterol Levels With Significant Lipoprotein Modifications and Without Clinical Atherosclerosis in an Italian Family," (1980), *J. Clin. Invest.*, 66, pp. 892-900.

Franceschini, G., et al., "Apolipoprotein A-I$_{MILANO}$: Correlation Between High Density Lipoprotein Subclass Distribution and Triglyceridemia," (1987), *Arteriosclerosis*, 7, pp. 426-435.

Franceschini, G., et al., "Apolipoprotein AI-Milano: Altered Lipid Binding Properties In A Human Apolipoprotein Variant," *Recent Aspects of Diagnals and Treatnent of Lipoprotein Disorders Impact on Prevention of Atherosclerotic Diseases*, (1986), pp. 73-80.

Francesehini, G., et al., "Relation Between the HDL Apoproteins and AI Isoproteins In Subjects With the AI$_{MILANO}$ Abnormality," (1981), *Metabolism*, 30(5), pp. 502-509.

Francone, O.L., et al., "Expression of Human Lecithin-Cholesterol Acyltransferase in Transgenic Mice: Effect of Human Apolipoprotein AI and Human Apolipoprotein AII on Plasma Lipoprotein Cholesterol Metabolism," (1995), *J. Clin. Invest.*, 96, pp. 1440-1448.

Gordon, D.J., et al., "High-Density Lipoprotein-The Clinical Implications of Recent Studies," (1989), *N. Eng. J. Med.*, 321, pp. 1311-1316.

Gordon, D.J., et al., "High-Density Lipoprotein Cholesterol and Cardiovascular Disease: Four Prospective American Studies", (1989), *Circulation*, 79(1), pp. 8-15.

Gordon, J.I., et al., "Biosynthesis Of Human Preapolipoprotein A-IV," (1984), *J. Biol. Chem.*, 259(1), pp. 468-474.

Gualandri, N., et al., "AI$_{Milano}$ Apoprotein Identification of the Complete Kindred and Evidence of a Dominant Genetic Transmission," (1985), *Am. J..Hum. Genet.*, 37, pp. 1083-1097.

Hoeg, J.M., et al., "Human Apolipoprotein A-I: Post-Translational Modification By Fatty Acid Acylation," (1986), *J. Biol. Chem.*, 261(9), pp. 3911-3914.

Holvoet, P., et al., "Phospholipid Binding and Lechithin-Cholesterol Acyltransferase Activation Properties of Apolipoprotein A-I Mutants," (1995), *Biochem.*, 34, pp. 13334-13342.

James, R.W., et al., "Modulated Serum Activities and Concentrations of Paraoxonase in High Density Lipoprotein Deficiency States," (1998), *Atherosclerosis*, 139, pp. 77-82.

Koizumi, J., et al., "Behavior of Human Apolipoprotein A-I: Phospholipid and apoHDL phospolipid Complexes in Vitro and After Injection into Rabbits", (1988), *J. Lipid. Res.*, 29, pp. 1405-1415.

Lackner, K.I, "Isoforms Of Apolipoprotein A-II In Human Plasma And Thoracic Duct Lymph: Identification Of Proapolipoprotein A-II and Sialic Acid-Containing Isoforms," (1985), *J. Biol. Chem.*, 260(2), pp. 703-706.

Li, D., et al., "Inhibition of Arterial Thrombus Formation by ApoAI Milano," (1999), *Arterioscler. Thromb. Vasc. Biol.*, 19, pp. 378-383.

Lin, A.C., et al., "Human Apolipoprotein A-I Prevents Atherosclerosis Associated with Apolipoprotein[a] in Transgenic Mice," (1994), *J. Lipid Res.*, 35, pp. 2263-2267.

Lund-Katz, S., et al., "Nuclear Magnetic Resonance Investigation of the Interations with Phospholipid of an Amphipathic or Helix-Forming Peptide of the Apolipoprotein Class," (1990), *J. Biol. Chem.*, 265(21), pp. 12217-12223.

Mezdour, H., et al., "Exogenous Supply of Artificial Lipoproteins Does not Decrease Susceptibility to Atherosclerosis in Cholesterol-Fed Rabbits," (19995), *Atherosclerosis*, 113, pp. 237-246.

Miller, N.E., et al., "Association of High-Density Lipoprotein Subclasses and Apolipoproteins with Ischemic Heart Disease and Coronary Atherosclerosis," (1987), *Amer. Heart*, 113, pp. 589-597.

Miyazaki, A., et al., "Intravenous Injection of Rabbit Apolipoprotein A-I Inhibits of the Progression of Atherosclerosis in Cholesterol-Fed Rabbits," (1995) *Arterioscler. Thromb. Vasc. Biol.*, 15(11), pp. 1882-1888.

Nanjee, M.N., et al., "Effects of Intravenous Infusion of Lipid-Free Apo A-J in Human," (1996), *Arterioscler. Thromb. Vasc. Biol.*, 16(9), pp. 1203-1214.

Nilsson, J., et al., "Lipoprotein-Like Phospholipid Particles Inhibit The Smooth Muscle Cell Cytotoxicity of Lysophosphatidycholine and Platelet-Activating Factor," (1998), *Arterioscler. Thromb. Vasc. Biol.*, 18, pp. 13-19.

Rosseneu, M., et al., "Physiological Significance of Apolipoprotein Mutants," (1995), *FASEB J*, 9, pp. 768-776.

Rubin, E.M., et al., "Inhibition of Early Atherogenesis in Transgenic Mice by Human Apolipoprotein AI," (1991), *Nature*, 353, pp. 265-267.

Segrest, J.P., et al., "A Molecular Theory of Lipid-Protein Interactions in the Plasma Lipoproteins", *FEBS Lett.*, (1994), 38(3), pp. 247-253.

Shah, P.K., et al., "Effects of Recombinant Apolipoprotein A-I$_{MILANO}$on Aortic Atherosclerosis in Apolipoprotein E-Deficient Mice," (1997), *Circulation*, 97, pp. 780-785.

Sirtori, C.R., et al., "Familial Disorders Of Plasma Apolipoproteins," (1985), *Klin Wochanschrift*, 63, pp. 481-489.

Lundberg & Suominen, "Incorporation of Cholesterol into Serum High Density Lipoprotein Apoprotein and Recombinants," *Chemistry and Physics of Lipids*, 34 (1987) 307-315.

Rea et al., "Rabbit Liver Apolipoprotein A-I Synthesis is Under Nonparenchymal Cell Paracine Control," *J. of Lipid Res.*, 35 (1994) 1274-1282.

Rodrigueza et al., "Large Versus Small Unilamellar Vesicles Mediate Reverse Cholesterol Transport In Vivo Into Two Distinct Hepatic Metabolic Pools: Implications for the Treatment of Atherosclerosis," *Arterioscler. Thromb.Vasc. Biol.* 17 (1997) 2132-2139.

European Patent Application EP 03734054, Supplementary Search Report dated May 27, 2009, 5 pages.

Carmena, R., "Statins: Monotherapy or Combination Strategy for the Treatment of Dyslipidemia", Heart Drug, Jan. 1, 2002, pp. 175-183, 2(4).

Eriksson, M., et al., "Stimulation of Fecal Steroid Excretion After Infusion of Recombinant Proapolipoprotein A-I: Potential Reverse Cholesterol Transport in Humans", Ciruclation, Aug. 10, 1999, pp. 594-598, 100(6).

JP 61-152632 English Translations, Publication date, Jul. 11, 1986.

Modrak, D.E., "Sphingomyelin Potentiates Chemotherapy of Human Cancer Xenografts", Biochemical and Biophysical Research Communications, Feb. 16, 2000, pp. 603-606, 268(2).

Schmelz, E.M., et al., "Sphingomyelin Consumption Suppresses Aberrant Colonic Crypt Foci and Increases the Proportion of Adenomas versus Adenocarcinomas in CF1 Mice Treated with 1,2-Dimethylhydrazine: Implications for Dietary Sphingolipids and Colon Carcinogenesis", Nov. 1, 1996, Cancer Research, pp. 4936-4941, 56(21).

Sirtori, C.R., et al., "Recombinant Apolipoproteins for the Treatment of Vascular Diseases," (1999), *Atherosclerosis*, 142, pp. 29-40.

Soma, M.R., et al., "Recombinant Apolipoprotein A-1$_{MILANO}$ Dimer Inhibits Carotid Intimal Thickening Induced By Perivascular Manipulation In Rabbits," (1995), *Circulation Res.*, 76, pp. 405-411.

Sparrow, J.T., et al., Ch. 10: "Lipid-Protein Interactions Structure-Function Relationships."

Sparrow, J.T., et al., "The Thermodynamics of Lipid-Protein Association and the Activation of Lecithin: Cholesterol Acyltransferase by Synthetic Lipopeptides", in *Peptides: Syntheses Structure-Function*, Roch& Gross, Eds., Pierce Chem, Co., Rockford, IL, pp. 253-256, (1981).

Spuhler, P., et al., "Binding of Apolipoprotein A-I Model Peptides in Lipid Bilayers," (1994), *J. Biol. Chem.*, 269(39), pp. 23904-23910.

Syvanne, M., et al., "Cholesterol Efflux from Fu5AH Hepatoma Cells Induced by Plasma of Subjects With or Without Coronary Artery Disease and Non-insulin-Dependent Diabetes: Importance of LpA-I:A-II Particles and Phospholipid Transfer Protein," (1996), *Atherosclerosis*, 127, pp. 245-253.

Thurberg, B.L., et al., "Lipoprotein Association Of Human Apolipoprotein E/A-I Chimeras: Expression In Transfected Hepatoma Cells," (1996), *J. Biol., Chem.*, 271, pp. 6062-6070.

Wang, G., et al., "Conformation of Human Serum Apolipoprotein A-I(166-185) in the Presence of Sodium Dodecyl Sulfate or Dodecylphosphocholine by H-NMR and CD. Evidence for Specific Peptide-SDS Interactions," (1996), *Biochim. Biophys.*, 1301, pp. 174-184.

Weisgraber, K.H., "Apolipoprotein E Distribution Among Human Plasma Lipoproteins: Role Of the Cysteine-Arginine Interchange At Residue 112," (1990), *J. Lipid. Res.*, 31, pp. 1503-1511.

Westman, J., et al., "Sterol 27-Hydroxylase- and ApoAI/ Phospholipid-Mediated Efflux of Cholesterol From Cholesterol- Laden Macrophages: Evidence for an Inverse Relation Between the Two Mechanisms," (1998), *Arterioscler. Thromb. Vasc. Biol.*, 18, pp. 554-561.

Windler et al., "The Estradiol-Stimulated Lipoprotein Receptor Of Rat Liver: A Binding Site That Mediates the Uptake of Rate Lipoproteins Containing Apoproteins B and E", (1980), *J. Biol. Chem.*, 255 (21), pp. 10464-10471

\* cited by examiner

METHOD OF TREATING DYSLIPIDEMIC DISORDER

This application is a divisional of U.S. application Ser. No. 10/440,213, filed May 16, 2003, now abandoned, which claims priority of U.S. Provisional Application Ser. No. 60/381,512, filed May 17, 2002, incorporated herein by reference in its entirety.

1. TECHNICAL FIELD

The invention provides methods of treating or preventing a disease, condition or disorder associated with dyslipidemia with apolipoprotein-sphingomyelin complexes or pharmaceutical compositions thereof. The invention further provides compositions for treating or preventing a disease, condition or disorder associated with dyslipidemia and methods for the production of the compositions.

2. BACKGROUND OF THE INVENTION

Circulating cholesterol is carried by plasma lipoproteins—complex particles of lipid and protein composition that transport lipids in the blood. Four major classes of lipoprotein particles circulate in plasma and are involved in the fat-transport system: chylomicrons, very low density lipoprotein (VLDL), low density lipoprotein (LDL) and high density lipoprotein (HDL). Chylomicrons constitute a short-lived product of intestinal fat absorption. VLDL and particularly, LDL, are responsible for the delivery of cholesterol from the liver (where it is synthesized or obtained from dietary sources) to extrahepatic tissues, including the arterial walls. HDL, by contrast, mediates reverse cholesterol transport (RCT), the removal of cholesterol from extrahepatic tissues to the liver, where it is catabolized, eliminated or recycled. HDL also plays a role in inflammation, transporting oxidized lipids and interleukin.

Lipoprotein particles have a hydrophobic core comprised of cholesterol (normally in the form of a cholesteryl ester) and triglycerides. The core is surrounded by a surface coat comprising phospholipids, unesterified cholesterol and apolipoproteins. Apolipoproteins mediate lipid transport, and some may interact with enzymes involved in lipid metabolism. At least ten apolipoproteins have been identified, including: ApoA-I, ApoA-II, ApoA-IV, ApoA-V, ApoB, ApoC-I, ApoC-II, ApoC-III, ApoD, ApoE, ApoJ and ApoH. Other proteins such as LCAT (lecithin:cholesterol acyltransferase), CETP (cholesteryl ester transfer protein), PLTP (phospholipid transfer protein) and PON (paraoxonase) are also found associated with lipoproteins.

Cardiovascular diseases such as coronary heart disease, coronary artery disease and atherosclerosis are linked overwhelmingly to elevated serum cholesterol levels. For example, atherosclerosis is a slowly progressive disease characterized by the accumulation of cholesterol within the arterial wall. Compelling evidence supports the theory that lipids deposited in atherosclerotic lesions are derived primarily from plasma LDLs; thus, LDLs have popularly become known as "bad" cholesterol. In contrast, HDL serum levels correlate inversely with coronary heart disease. Indeed, high serum levels of HDLs are regarded as a negative risk factor. It is hypothesized that high levels of plasma HDLs are not only protective against coronary artery disease, but may actually induce regression of atherosclerotic plaque (see, e.g., Badimon et al., 1992, *Circulation* 86(Suppl. III):86-94; Dansky and Fisher, 1999, *Circulation* 100:1762-63; Tangirala et al., 1999, *Circulation* 100(17):1816-22; Fan et al., 1999, *Atherosclerosis* 147(1):139-45; Deckert et al., 1999, *Circulation* 100(11):1230-35; Boisvert et al., 1999, *Arterioscler. Thromb. Vasc. Biol.* 19(3):525-30; Benoit et al., 1999, *Circulation* 99(1):105-10; Holvoet et al.; 1998, *J. Clin. Invest.* 102(2): 379-85; Duverger et al., 1996, *Circulation* 94(4):713-17; Miyazaki et al., 1995, *Arterioscler. Thromb. Vasc. Biol.* 15(11):1882-88; Mezdour et al., 1995, *Atherosclerosis* 113 (2):237-46; Liu et al., 1994, *J. Lipid Res.* 35(12):2263-67; Plump et al., 1994, *Proc. Nat. Acad. Sci. USA* 91(20):9607-11; Paszty et al., 1994, *J. Clin. Invest* 94(2):899-903; She et al., 1992, *Chin. Med. J.* (Engl). 105(5):369-73; Rubin et al., 1991, *Nature* 353(6341):265-67; She et al., 1990, *Ann. NY Acad. Sci.* 598:339-51; Ran, 1989, *Chung Hua Ping Li Hsueh Tsa Chih* (also translated as: *Zhonghua Bing Li Xue Za Zhi*) 18(4):257-61; Quezado et al., 1995, *J. Pharmacol. Exp. Ther.* 272(2):604-11; Duverger et al., 1996, *Arterioscler. Thromb. Vasc. Biol.* 16(12):1424-29; Kopfler et al., 1994, *Circulation;* 90(3):1319-27; Miller et al., 1985, *Nature* 314(6006):109-11; Ha et al., 1992, *Biochim. Biophys. Acta* 1125(2):223-29; Beitz et al., 1992, *Prostaglandins Leukot. Essent. Fatty Acids* 47(2): 149-52). As a consequence, HDLs have popularly become known as "good" cholesterol.

The "protective" role of HDL has been confirmed in a number of studies (e.g., Miller et al., 1977, *Lancet* 1(8019): 965-68; Whayne et al., 1981, *Atherosclerosis* 39:411-19). In these studies, the elevated levels of LDL appear to be associated with increased cardiovascular risk, whereas high HDL levels seem to confer cardiovascular protection. In vivo studies have further demonstrated the protective role of HDL, showing that HDL infusions into rabbits may hinder the development of cholesterol induced arterial lesions (Badimon et al., 1989, *Lab. Invest.* 60:455-61) and/or induce their regression (Badimon et al., 1990, *J. Clin. Invest.* 85:1234-41).

2.1. Reverse Cholesterol Transport, HDL and Apolipoprotein A-I

The reverse cholesterol transport (RCT) pathway functions to eliminate cholesterol from most extrahepatic tissues and is crucial to maintaining the structure and function of most cells in the body. RCT consists mainly of three steps: (a) cholesterol efflux, i.e., the initial removal of cholesterol from various pools of peripheral cells; (b) cholesterol esterification by the action of lecithin:cholesterol acyltransferase (LCAT), preventing a re-entry of effluxed cholesterol into cells; and (c) uptake of HDL cholesterol and cholesteryl esters to liver cells for hydrolysis, then recycling, storage, excretion in bile or catabolism to bile acids.

LCAT, the key enzyme in RCT, is produced by the liver and circulates in plasma associated with the HDL fraction. LCAT converts cell-derived cholesterol to cholesteryl esters, which are sequestered in HDL destined for removal (see Jonas 2000, *Biochim. Biophys. Acta* 1529(1-3):245-56). Cholesteryl ester transfer protein (CETP) and phospholipid transfer protein (PLTP) contribute to further remodeling of the circulating HDL population. CETP moves cholesteryl esters made by LCAT to other lipoproteins, particularly ApoB-comprising lipoproteins, such as VLDL and LDL. PLTP supplies lecithin to HDL. HDL triglycerides are catabolized by the extracellular hepatic triglyceride lipase, and lipoprotein cholesterol is removed by the liver via several mechanisms.

The functional characteristics of HDL particles are mainly determined by their major apolipoprotein components such as ApoA-I and ApoA-II. Minor amounts of ApoC-I, ApoC-II, ApoC-III, ApoD, ApoA-IV, ApoE, ApoJ have also been observed associated with HDL. HDL exists in a wide variety of different sizes and different mixtures of the above-mentioned constituents, depending on the status of remodeling during the metabolic RCT cascade or pathway.

Each HDL particle usually comprises at least one molecule, and usually two to four molecules, of ApoA-I. HDL particles may also comprise only ApoE (γ-LpE particles), which are known to also be responsible for cholesterol efflux, as described by Prof. Gerd Assmann (see, e.g., von Eckardstein et al., 1994, *Curr Opin Lipidol.* 5(6):404-16). ApoA-I is synthesized by the liver and small intestine as preproapolipoprotein A-I, which is secreted as proapolipoprotein A-I (proApoA-I) and rapidly cleaved to generate the plasma form of ApoA-I, a single polypeptide chain of 243 amino acids (Brewer et al., 1978, *Biochem. Biophys. Res. Commun.* 80:623-30). PreproApoA-I that is injected experimentally directly into the bloodstream is also cleaved into the plasma form of ApoA-I (Klon et al., 2000, *Biophys. J.* 79(3):1679-85; Segrest et al., 2000, *Curr. Opin. Lipidol.* 11(2):105-15; Segrest et al., 1999, *J. Biol. Chem.* 274 (45):31755-58).

ApoA-I comprises 6 to 8 different 22-amino acid α-helices or functional repeats spaced by a linker moiety that is frequently proline. The repeat units exist in amphipathic helical conformation (Segrest et al., 1974, *FEBS Lett.* 38: 247-53) and confer the main biological activities of ApoA-I, i.e., lipid binding and lecithin cholesterol acyl transferase (LCAT) activation.

ApoA-I forms three types of stable complexes with lipids: small, lipid-poor complexes referred to as pre-β-1 HDL; flattened discoidal particles comprising polar lipids (phospholipid and cholesterol) referred to as pre-β-2 HDL; and spherical particles, comprising both polar and nonpolar lipids, referred to as spherical or mature HDL ($HDL_{L3}$ and $HDL_{L2}$). Most HDL in the circulating population comprise both ApoA-I and ApoA-II (the "AI/AII-HDL fraction"). However, the fraction of HDL comprising only ApoA-I (the "AI-HDL fraction") appears to be more effective in RCT. Certain epidemiologic studies support the hypothesis that the ApoA-I-HDL fraction is anti-atherogenic. (Parra et al., 1992, *Arterioscler. Thromb.* 12:701-07; Decossin et al., 1997, *Eur. J. Clin. Invest.* 27:299-307).

Although the mechanism for cholesterol transfer from the cell surface (i.e., cholesterol efflux) is unknown, it is believed that the lipid-poor complex, pre-β-1 HDL, is the preferred acceptor for cholesterol transferred from peripheral tissue involved in RCT. (See Davidson et al., 1994, *J. Biol. Chem.* 269:22975-82; Bielicki et al., 1992, *J. Lipid Res.* 33:1699-1709; Rothblat et al., 1992, *J. Lipid Res.* 33:1091-97; and Kawano et al., 1993, *Biochemistry* 32:5025-28; Kawano et al., 1997, *Biochemistry* 36:9816-25). During this process of cholesterol recruitment from the cell surface, pre-β-1 HDL is rapidly converted to pre-β-2 HDL. PLTP may increase the rate of pre-β-2 HDL disc formation, but data indicating a role for PLTP in RCT is lacking. LCAT reacts preferentially with discoidal, small (pre-β) and spherical (i.e., mature) HDL, transferring the 2-acyl group of lecithin or other phospholipids to the free hydroxyl residue of cholesterol to generate cholesteryl esters (retained in the HDL) and lysolecithin. The LCAT reaction requires ApoA-I as an activator; i.e., ApoA-I is the natural cofactor for LCAT. The conversion of cholesterol sequestered in the HDL to its ester prevents re-entry of cholesterol into the cell, the net result being that cholesterol is removed from the cell.

Cholesteryl esters in the mature HDL particles in the ApoAI-HDL fraction (i.e., comprising ApoA-I and no ApoA-II) are removed by the liver and processed into bile more effectively than those derived from HDL comprising both ApoA-I and ApoA-II (the AI/AII-HDL fraction). This may be owing, in part, to the more effective binding of ApoAI-HDL to the hepatocyte membrane. The existence of an HDL receptor has been hypothesized, and a scavenger receptor, class B, type I (SR-BI) has been identified as an HDL receptor (Acton et al., 1996, *Science* 271:518-20; Xu et al., 1997, *Lipid Res.* 38:1289-98). SR-BI is expressed most abundantly in steroidogenic tissues (e.g., the adrenals), and in the liver (Landschulz et al., 1996, *J. Clin. Invest.* 98:984-95; Rigotti et al., 1996, *J. Biol. Chem.* 271:33545-49).

CETP may also play a role in RCT. Changes in CETP activity or its acceptors, VLDL and LDL, play a role in "remodeling" the HDL population. For example, in the absence of CETP, the HDLs become enlarged particles that are not cleared. (For reviews of RCT and HDLs, see Fielding and Fielding, 1995, *J. Lipid Res.* 36:211-28; Barrans et al., 1996, *Biochem. Biophys. Acta* 1300:73-85; Hirano et al., 1997, *Arterioscler. Thromb. Vasc. Biol.* 17(6):1053-59).

HDL also plays a role in the reverse transport of other lipids and in detoxification, i.e., the transport of lipids from cells, organs, and tissues to the liver for catabolism and excretion. Such lipids include sphingomyelin (SM), oxidized lipids, and lysophophatidylcholine. For example, Robins and Fasulo (1997, *J. Clin. Invest.* 99:380-84) have shown that HDLs stimulate the transport of plant sterol by the liver into bile secretions.

The major component of HDL, ApoA-I, can associate with SM in vitro. When ApoA-I is reconstituted in vitro with bovine brain SM (BBSM), a maximum rate of reconstitution occurs at 28° C., the temperature approximating the phase transition temperature for BBSM (Swaney, 1983, *J. Biol. Chem.* 258(2), 1254-59). At BBSM:ApoA-I ratios of 7.5:1 or less (wt/wt), a single reconstituted homogeneous HDL particle is formed that comprises three ApoA-I molecules per particle and that has a BBSM:ApoA-I molar ratio of 360:1. It appears in the electron microscope as a discoidal complex similar to that obtained by recombination of ApoA-I with phosphatidylcholine at elevated ratios of phospholipid/protein. At BBSM:ApoA-I ratios of 15:1 (wt/wt), however, larger-diameter discoidal complexes form that have a higher phospholipid:protein molar ratio (535:1). These complexes are significantly larger, more stable, and more resistant to denaturation than ApoA-I complexes formed with phosphatidylcholine.

Sphingomyelin (SM) is elevated in early cholesterol acceptors (pre-β-HDL and γ-migrating ApoE-comprising lipoprotein), suggesting that SM might enhance the ability of these particles to promote cholesterol efflux (Dass and Jessup 2000, *J. Pharm. Pharmacol.* 52:731-61; Huang et al., 1994, *Proc. Natl. Acad. Sci. USA* 91:1834-38; Fielding and Fielding 1995, *J. Lipid Res.* 36:211-28).

2.2. Protective Mechanism of HDL and ApoA-I

Recent studies of the protective mechanism(s) of HDL have focused on apolipoprotein A-I (ApoA-I), the major component of HDL. High plasma levels of ApoA-I are associated with absence or reduction of coronary lesions (Maciejko et al., 1983, *N. Engl. J. Med.* 309:385-89; Sedlis et al., 1986, *Circulation* 73:978-84).

The infusion of ApoA-I or of HDL in experimental animals exerts significant biochemical changes, as well as reduces the extent and severity of atherosclerotic lesions. After an initial report by Maciejko and Mao (1982, *Arteriosclerosis* 2:407a), Badimon et al., (1989, *Lab. Invest.* 60:455-61; 1989, *J. Clin. Invest.* 85:1234-41) found that they could significantly reduce the extent of atherosclerotic lesions (reduction of 45%) and their cholesterol ester content (reduction of 58.5%) in cholesterol-fed rabbits, by infusing HDL (d=1.063-1.325 g/ml). They also found that the infusions of HDL led to a close to a 50% regression of established lesions. Esper et al. (1987, *Arteriosclerosis* 7:523a) have shown that infusions of HDL can markedly change the plasma lipoprotein composition of Watanabe rabbits with inherited hypercholesterolemia, which develop early arterial lesions. In these rabbits, HDL infusions can more than double the ratio between the protective HDL and the atherogenic LDL.

The potential of HDL to prevent arterial disease in animal models has been further underscored by the observation that ApoA-I can exert a fibrinolytic activity in vitro (Saku et al., 1985, *Thromb. Res.* 39:1-8). Ronneberger (1987, Xth Int. Congr. Pharmacol., Sydney, 990) demonstrated that ApoA-I can increase fibrinolysis in beagle dogs and in Cynomologous monkeys. A similar activity can be noted in vitro on human plasma. Ronneberger was able to confirm a reduction of lipid deposition and arterial plaque formation in ApoA-I treated animals.

In vitro studies indicate that complexes of ApoA-I and lecithin can promote the efflux of free cholesterol from cultured arterial smooth muscle cells (Stein et al., 1975, *Biochem. Biophys. Acta*, 380:106-18). By this mechanism, HDL can also reduce the proliferation of these cells (Yoshida et al., 1984, *Exp. Mol. Pathol.* 41:258-66).

Two naturally occurring human mutations of ApoA-I have been isolated in which an arginine residue is mutated to cysteine. In apolipoprotein A-$I_{Milano}$ (ApoA-$I_M$), this substitution occurs at residue 173, whereas in apolipoprotein A-$I_{Paris}$ (ApoA-$I_P$), this substitution occurs at residue 151 (Franceschini et al., 1980, *J. Clin. Invest.* 66:892-900; Weisgraber et al., 1983, *J. Biol. Chem.* 258:2508-13; Bruckert et al., 1997, *Atherosclerosis* 128:121-28; Daum et al., 1999, *J. Mol. Med.* 77:614-22; Klon et al., 2000, *Biophys. J.* 79(3): 1679-85).

Reconstituted HDL particles comprising disulfide-linked homodimers of either ApoA-$I_M$ or ApoA-$I_P$ are similar to reconstituted HDL particles comprising wild-type ApoA-I in their ability to clear dimyristoylphosphatidylcholine (DMPC) emulsions and their ability to promote cholesterol efflux (Calabresi et al., 1997b, *Biochemistry* 36:12428-33; Franceschini et al., 1999, *Arterioscler. Thromb. Vasc. Biol.* 19:1257-62; Daum et al., 1999, *J. Mol. Med.* 77:614-22). In both mutations, heterozygous individuals have decreased levels of HDL but paradoxically, are at a reduced risk for atherosclerosis (Franceschini et al., 1980, *J. Clin. Invest.* 66:892-900; Weisgraber et al., 1983, *J. Biol. Chem.* 258:2508-13; Bruckert et al., 1997, *Atherosclerosis* 128:121-28). Reconstituted HDL particles comprising either variant are capable of LCAT activation, although with decreased efficiency when compared with reconstituted HDL particles comprising wild-type ApoA-I (Calabresi et al., 1997a, *Biochem. Biophys. Res. Commun.* 232:345-49; Daum et al., 1999, *J. Mol. Med.* 77:614-22).

The ApoA-$I_M$ mutation is transmitted as an autosomal dominant trait; 8 generations of carriers within a family have been identified (Gualandri et al., 1984, *Am. J. Hum. Genet.* 37:1083-97). The status of an ApoA-$I_M$ carrier individual is characterized by a remarkable reduction in HDL-cholesterol level. In spite of this, carrier individuals do not apparently show any increased risk of arterial disease. Indeed, by examination of genealogical records, it appears that these subjects may be "protected" from atherosclerosis (Sirtori et al., 2001, *Circulation*, 103: 1949-1954; Roma et al., 1993, *J. Clin. Invest.* 91(4):1445-520).

The mechanism of the possible protective effect of ApoA-$I_M$ in carriers of the mutation seems to be linked to a modification in the structure of the mutant ApoA-$I_M$, with loss of one alpha-helix and an increased exposure of hydrophobic residues (Franceschini et al., 1985, *J. Biol. Chem.* 260:1632-35). The loss of the tight structure of the multiple alpha-helices leads to an increased flexibility of the molecule, which associates more readily with lipids, compared to normal ApoA-I. Moreover, apolipoprotein-lipid complexes are more susceptible to denaturation, thus suggesting that lipid delivery is also improved in the case of the mutant.

Bielicki, et al. (1997, *Arterioscler. Thromb. Vasc. Biol.* 17 (9):1637-43) has demonstrated that ApoA-$I_M$ has a limited capacity to recruit membrane cholesterol compared with wild-type ApoA-I. In addition, nascent HDL formed by the association of ApoA-$I_M$ with membrane lipids was predominantly 7.4-nm particles rather than larger 9- and 11-nm complexes formed by wild-type ApoA-I. These observations indicate that the $Arg_{173} \rightarrow Cys_{173}$ substitution in the ApoA-I primary sequence interfered with the normal process of cellular cholesterol recruitment and nascent HDL assembly. The mutation is apparently associated with a decreased efficiency for cholesterol removal from cells. Its antiatherogenic properties may therefore be unrelated to RCT.

The most striking structural change attributed to the $Arg_{173} \rightarrow Cys_{173}$ substitution is the dimerization of ApoA-$I_M$ (Bielicki et al., 1997, *Arterioscler. Thromb. Vasc. Biol.* 17 (9):1637-43). ApoA-$I_M$ can form homodimers with itself and heterodimers with ApoA-II. Studies of blood fractions comprising a mixture of apolipoproteins indicate that the presence of dimers and complexes in the circulation may be responsible for an increased elimination half-life of apolipoproteins. Such an increased elimination half-life has been observed in clinical studies of carriers of the mutation (Gregg et al., 1988, NATO ARW on Human Apolipoprotein Mutants: From Gene Structure to Phenotypic Expression, Limone SG). Other studies indicate that ApoA-$I_M$ dimers (ApoA-$I_M$/ApoA-$I_M$) act as an inhibiting factor in the interconversion of HDL particles in vitro (Franceschini et al., 1990, *J. Biol. Chem.* 265:12224-31).

2.3. Current Treatments for Dyslipidemic and Related Disorders

Dyslipidemic disorders are diseases associated with elevated serum cholesterol and triglyceride levels and lowered serum HDL:LDL ratios, and include hyperlipidemia, especially hypercholesterolemia, coronary heart disease, coronary artery disease, vascular and perivascular diseases, and cardiovascular diseases such as atherosclerosis. Syndromes associated with atherosclerosis such as intermittent claudication, caused by arterial insufficiency, are also included. A number of treatments are currently available for lowering the elevated serum cholesterol and triglycerides associated with dyslipidemic disorders. However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), and colestipol hydrochloride (Colestid®, The Upjohn Company). When taken orally, these positively-charged resins bind to the negatively charged bile acids in the intestine. Because the resins cannot be absorbed from the intestine, they are excreted carrying the bile acids with them. The use of such resins at best, however, only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

Statins are cholesterol lowering agents that block cholesterol synthesis by inhibiting HMGCoA reductase—the key enzyme involved in the cholesterol biosynthetic pathway. Statins, e.g., lovastatin (Mevacor®), simvastatin (Zocor®), pravastatin (Pravachol®), fluvastatin (Lescol®) and atorvastatin (Lipitor®), are sometimes used in combination with bile-acid-binding resins. Statins significantly reduce serum cholesterol and LDL-serum levels, and slow progression of coronary atherosclerosis. However, serum HDL cholesterol levels are only moderately increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (*The Physicians Desk Reference*(56$^{th}$ ed., 2002) Medical Economics).

Niacin (nicotinic acid) is a water soluble vitamin B-complex used as a dietary supplement and antihyperlipidemic agent. Niacin diminishes production of VLDL and is effective at lowering LDL. In some cases, it is used in combination with bile-acid binding resins. Niacin can increase HDL when used at adequate doses, however, its usefulness is limited by serious side effects when used at such high doses. Niaspan® is a form of extended-release niacin that produces fewer side effects than pure niacin. Niacin/Lovastatin (Nicostatin®) is a formulation containing both niacin and lovastatin and combines the benefits of each drug.

Fibrates are a class of lipid-lowering drugs used to treat various forms of hyperlipidemia (i.e., elevated serum triglycerides) that may also be associated with hypercholesterolemia. Fibrates appear to reduce the VLDL fraction and modestly increase HDL—however the effects of these drugs on serum cholesterol is variable. In the United States, fibrates such as clofibrate (Atromid-S®), fenofibrate (Tricor®) and bezafibrate (Bezalip®) have been approved for use as antilipidemic drugs, but have not received approval as hypercholesterolemia agents. For example, clofibrate is an antilipidemic agent that acts (via an unknown mechanism) to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®) is a lipid regulating agent that moderately decreases serum triglycerides and VLDL cholesterol, and moderately increases HDL cholesterol—the $HDL_2$ and $HDL_3$ subfractions as well as both ApoA-I and A-II (i.e., the AI/AII-HDL fraction). However, the lipid response is heterogeneous, especially among different patient populations. Moreover, while prevention of coronary heart disease was observed in male patients between 40-55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates including toxicity such as malignancy, (especially gastrointestinal cancer), gallbladder disease and an increased incidence in non-coronary mortality. These drugs are not indicated for the treatment of patients with high LDL or low HDL as their only lipid abnormality (*The Physicians Desk Reference* (56$^{th}$ ed., 2002) Medical Economics). Oral estrogen replacement therapy may be considered for moderate hypercholesterolemia in post-menopausal women. However, increases in HDL may be accompanied with an increase in triglycerides. Estrogen treatment is, of course, limited to a specific patient population (postmenopausal women) and is associated with serious side effects including induction of malignant neoplasms, gall bladder disease, thromboembolic disease, hepatic adenoma, elevated blood pressure, glucose intolerance, and hypercalcemia.

The need therefore exists for safer drugs that are more efficacious in lowering serum cholesterol, increasing HDL serum levels, preventing and/or treating diseases, conditions or disorders associated with dyslipidemia.

For example, HDL, as well as recombinant forms of ApoA-I complexed with phospholipids can serve as sinks/scavengers for apolar or amphipathic molecules, e.g., cholesterol and derivatives (oxysterols, oxidized sterols, plant sterols, etc.), cholesterol esters, phospholipids and derivatives (oxidized phospholipids), triglycerides, oxidation products, and lipopolysaccharides (LPS) (see, e.g., Casas et al., 1995, *J. Surg. Res.* November; 59(5):544-52). HDL can also serve as also a scavenger for TNF-α and other lymphokines. HDL can also serve as a carrier for human serum paraoxonases, e.g., PON-1, -2, -3. Paraoxonase, an esterase associated with HDL, is important for protecting cell components against oxidation. Oxidation of LDL, which occurs during oxidative stress, appears directly linked to development of atherosclerosis (Aviram, 2000, *Free Radic. Res.* 33 Suppl:S85-97). Paraoxonase appears to play a role in susceptibility to atherosclerosis and cardiovascular disease (Aviram, 1999, *Mol. Med. Today* 5(9):381-86). Human serum paraoxonase (PON-1) is bound to high-density lipoproteins (HDLs). Its activity is inversely related to atherosclerosis. PON-1 hydrolyzes organophosphates and may protect against atherosclerosis by inhibition of the oxidation of HDL and low-density lipoprotein (LDL) (Aviram, 1999, *Mol. Med. Today* 5(9):381-86). Experimental studies suggest that this protection is associated with the ability of PON-1 to hydrolyze specific lipid peroxides in oxidized lipoproteins. Interventions that preserve or enhance PON-1 activity may help to delay the onset of atherosclerosis and coronary heart disease.

HDL further has a role as an antithrombotic agent and fibrinogen reducer, and as an agent in hemorrhagic shock (Cockerill et al., WO 01/13939, published Mar. 1, 2001). HDL, and ApoA-I in particular, has been show to facilitate an exchange of lipopolysaccharide produced by sepsis into lipid particles comprising ApoA-I, resulting in the functional neutralization of the lipopolysaccharide (Wright et al., WO9534289, published Dec. 21, 1995; Wright et al., U.S. Pat. No. 5,928,624 issued Jul. 27, 1999; Wright et al., U.S. Pat. No. 5,932,536, issued Aug. 3, 1999).

The therapeutic use of ApoA-I, ApoA-I$_{Milano}$, ApoA-I$_{Paris}$ and other variants, as well as reconstituted HDL, is presently limited, however, by the large amount of apolipoprotein required for therapeutic administration and by the cost of protein production, considering the low overall yield of production. It has been suggested by early clinical trials that the dose range is between 1.5-4 g of protein per infusion for treatment of cardiovascular diseases. The number of infusions required for a full treatment is unknown. (See. e.g., Eriksson et al., 1999, *Circulation* 100(6):594-98; Carlson, 1995, *Nutr. Metab. Cardiovasc. Dis.* 5:85-91; Nanjee et al., 2000, *Arterioscler. Thromb. Vasc. Biol.* 20(9):2148-55; Nanjee et al., 1999, *Arterioscler. Thromb. Vasc. Biol.* 19(4):979-89; Nanjee et al., 1996, *Arterioscler. Thromb. Vasc. Biol.* 16(9):1203-14). Thus, there is a need to develop new methods of treatment of dyslipidemic diseases, conditions or disorders that minimize the amount of apolipoprotein required for administration.

Citation or identification of any reference in Section 2 or in any other section of this application shall not be construed as an admission that such reference is available as prior art to the present invention.

3. SUMMARY OF THE INVENTION

The invention provides methods of treating or preventing a disease, condition or disorder associated with dyslipidemia, which methods utilize apolipoprotein-sphingomyelin complexes or compositions comprising apolipoprotein-sphingomyelin complexes, e.g., apolipoproteinA-I-SM (ApoA-I-SM).

Quite surprisingly, it has been discovered that when apolipoproteins such as ApoA-I are administered in the form of apolipoprotein-sphingomyelin ("Apo-SM") complexes, far less apolipoprotein is required to achieve the same or better cholesterol mobilization and, hence, therapeutic benefit, than that provided by other apolipoprotein-lipid complexes. For example, whereas soybean phosphatidylcholine ("soybeanPC") treatment regimens require administration of from 20-50 mg/kg (or 1-4 g/person) apolipoprotein every 2-5 days (i.v.), treatment regimens according to the invention require the administration of only 0.05 to 25 mg/kg (40 mg to 2 g per person) of apolipoprotein every 2-10 days (i.v.). Thus, the methods of the invention reduce by 2 to 25-fold the amount of apolipoprotein required for therapeutic benefit, thereby reducing substantially the cost of treatment, making the treatment regimen more convenient for the patient and perhaps reducing possible adverse effects associated with administration of the drug.

It has further been discovered that the mobilization of cholesterol (elevation of HDL-cholesterol above a baseline level before administration, wherein the baseline level is an initial level of HDL-cholesterol, or is a level known to one of skill in the art as a level that the patient in question would have, or an individual of the size and gender of the would have, prior to administration of a drug) is significantly sustained for a longer period of time for proApoA-I-SM complexes, i.e., longer than that of conventional apolipoprotein-phospholipid complexes. Thus, treatments according to the invention may be less frequent than current treatment protocols, typically about every 2 to 10 days, as compared with about every 2 to 5 days, without loss of therapeutic benefit. Furthermore, a decreased dose may be administered with the same frequency. In many embodiments, administration is about every 5 to 10 days, significantly reducing the number of clinic or hospital visits required by the patient.

The invention encompasses, in one embodiment, a pharmaceutically acceptable and injectable unit dosage which comprises less than 3500 mg of an apolipoprotein-sphingomyelin complex. In alternative embodiments, the composition comprises less than 1750 mg, less than 1400 mg, less than 700 mg and less than 350 mg per unit dosage form.

Use of the ApoA-I-SM complexes according to the invention is also advantageous because lower anticipated doses of the volume of ApoA-I-SM complexes infused or injected leads to faster and easier administration and improved patient comfort.

Use of the ApoA-I-SM complexes according to the invention is further advantageous because SM is a much more chemically stable lipid than soybean phosphatidylcholine (soybean PC), hence there is greater stability of ApoA-I complexes and longer product shelf-life compared to convention complexes.

The methods of the invention provide benefit in virtually any context in which apolipoprotein therapy is advantageous. For example, the methods of the invention may be advantageously used to treat or prevent virtually any disease, condition or disorder associated with dyslipidemia that is treatable with apolipoproteins. Using the methods of the invention, a dosage of apolipoprotein from 2- to 25-fold less than the effective dosage of apolipoprotein alone, or apolipoprotein and soybean PC, may be administered. Since Apo-SM complexes are administered systemically, they can be used to treat or prevent atherosclerosis and stenosis, mobilizing cholesterol from a patient's entire vasculature including small vessels.

4. DESCRIPTION OF THE FIGURES

FIG. 1 shows absolute changes in levels of HDL fraction of unesterified cholesterol following administration of 15 mg/kg doses of r-proApoA-I-SM and r-proApoA-I-POPC complexes. X-axis: time (hours). Y-axis: Change in free HDL cholesterol (mg/dL).

5. DETAILED DESCRIPTION OF THE INVENTION

The invention provides methods of treating or preventing a disease, condition or disorder associated with dyslipidemia utilizing apolipoprotein-sphingomyelin complexes or pharmaceutical compositions comprising apolipoprotein-sphingomyelin ("Apo-SM") complexes, e.g., apolipoproteinA-I-SM (ApoA-I-SM).

As used herein, the terms "dyslipidemia" or "dyslipidemic" refer to an abnormally elevated or decreased level of lipid in the blood plasma, including, but not limited to, the altered level of lipid associated with the following conditions: coronary heart disease; coronary artery disease; cardiovascular disease, hypertension, restenosis, vascular or perivascular diseases; dyslipidemic disorders; dyslipoproteinemia; high levels of low density lipoprotein cholesterol; high levels of very low density lipoprotein cholesterol; low levels of high density lipoproteins; high levels of lipoprotein Lp(a) cholesterol; high levels of apolipoprotein B; atherosclerosis (including treatment and prevention of atherosclerosis); hyperlipidemia; hypercholesterolemia; familial hypercholesterolemia (FH); familial combined hyperlipidemia (FCH); lipoprotein lipase deficiencies, such as hypertriglyceridemia, hypoalphalipoproteinemia, and hypercholesterolemialipoprotein. Quite surprisingly, it has been discovered that when apolipoproteins such as Apo-AI are administered in the form of apolipoprotein-sphingomyelin (Apo-SM) complexes, far less apolipoprotein is required to achieve the same or better cholesterol mobilization and, hence, therapeutic benefit, than that provided by apolipoprotein-lipid complexes of phosphatidylcholines such as soybeanPC.

The invention encompasses the treatment of diseases or disorders associated with dyslipidemia in a human in need thereof which comprises administering a therapeutically effective amount of an apolipoprotein-sphingomyelin complex to said human. Preferably the complex is a solid, including a lyophilized solid, suitable for reconstitution into a solution of apolipoprotein-sphingomyelin discoidal particles. The administration is preferably parenteral, especially intravenous, bolus injection, intramuscular, subcutaneous and the like. Thus, the methods of the invention use 2- to 25-fold less apolipoprotein than is required when a complex of apolipoprotein and soybean PC is administered.

It has further been discovered that the mobilization of cholesterol (elevation of HDL-cholesterol above the baseline (initial) level before administration) is sustained for a longer period of time for proApoA-I-SM complexes than that of apolipoprotein-phosphatidylcholine complexes. Thus, treatments according to the invention may be applied less frequently, typically about every 2 to 10 days, without loss of therapeutic benefit. Furthermore, a decreased dose may be administered with the same frequency. In many embodiments, treatment may be applied every 5 to 10 days, significantly reducing the number of clinic or hospital visits required by the patient.

Use of the ApoA-I-SM complexes according to the invention is also advantageous because lower anticipated doses of the volume of ApoA-I-SM complexes infused or injected leads to faster and easier administration and improved patient comfort.

Use of the ApoA-I-SM complexes according to the invention is further advantageous because SM is a much more chemically stable lipid than soybean phosphatidylcholine (soybean PC), hence there is greater stability of ApoA-I complexes and longer product shelf-life compared to convention complexes.

The administration methods of the invention provide benefit in virtually any context in which apolipoprotein therapy is advantageous. For example, the methods of the invention may be advantageously used to treat or prevent virtually any disease, condition or disorder associated with dyslipidemia, or symptom thereof, responsive to apolipoproteins. Using the methods of the invention, a dosage of apolipoprotein from 2- to 25-fold less than the effective dosage currently known in the art would be expected to be efficacious in treating or preventing the disease or in bringing about an ameliorative effect. Since Apo-SM complexes are administered systemically, they can be used to treat or prevent atherosclerosis and stenosis, mobilizing cholesterol from a patient's entire vasculature including small vessels.

The invention is illustrated by working examples that demonstrate that the ApoA-I-SM complexes of the invention can increase the concentration of HDL and increase cellular cholesterol efflux. Use of the ApoA-I-SM complexes disclosed herein in vivo in animal models results in an increase of HDL cholesterol levels in plasma, which is an indicative of cholesterol mobilization/efflux by recombinant HDL particles (i.e., ApoAI-SM-complexes). In addition, the increase of HDL cholesterol concentration induced by injection of ApoAI-SM particles is significantly greater than that induced by ApoAI-phosphatidylcholine particles (such as ApoAI-SoybeanPC and ApoAI-POPC).

For clarity of disclosure, and not by way of limitation, the detailed description of the invention is divided into the subsections set forth below.

5.1. Apolipoproteins and Apolipoprotein Peptides

The invention utilizes apolipoprotein compositions in which an apolipoprotein is complexed with sphingomyelin ("Apo-SM complexes").

Virtually any apolipoprotein or apolipoprotein derivative or analogue that provides therapeutic benefit when used to treat or prevent the above-listed disorders may be complexed with SM and advantageously administered at lower than conventional doses according to the invention. Further, any protein or peptide of an α-helical nature that also activates LCAT may be used. Suitable apolipoproteins include, but are not limited to, preproapolipoprotein forms of ApoA-I, ApoA-II, ApoA-IV, ApoA-V and ApoE; pro- and mature forms of human ApoA-I, ApoA-II, ApoA-IV, and ApoE; and active polymorphic forms, isoforms, variants and mutants as well as truncated forms, the most common of which are ApoA-I$_{Milano}$ (ApoA-I$_M$) and ApoA-I$_{Paris}$ (ApoA-I$_P$). Homo- and heterodimers (where feasible) of pro- and mature ApoA-I (Duverger et al., 1996, *Arterioscler. Thromb. Vasc. Biol.* 16(12): 1424-29) ApoA-I$_M$ (Franceschini et al., 1985, *J. Biol. Chem.* 260:1632-35), ApoA-I$_{Paris}$ is (Daum et al., 1999, *J. Mol. Med.* 77:614-22), ApoA-II (Shelness et al., 1985, *J. Biol. Chem.* 260(14):8637-46; Shelness et al., 1984, *J. Biol. Chem.* 259 (15):9929-35), ApoA-IV (Duverger et al., 1991, *Euro. J. Biochem.* 201(2):373-83), ApoE (McLean et al., 1983, *J. Biol. Chem.* 258(14):8993-9000), ApoJ and ApoH may also be utilized within the scope of the invention. Apolipoproteins utilized by the invention also include recombinant or purified apolipoproteins. Apolipoprotein-SM complexes that may be used according to the methods of the invention include those disclosed in U.S. Pat. No. 6,287,590, issued Sep. 11, 2001, which is incorporated herein by reference in its entirety.

Methods for obtaining apolipoproteins utilized by the invention are well-known in the art, see, e.g., Chung et al., 1980, *J. Lipid Res.* 21(3):284-91; Cheung et al., 1987, *J. Lipid Res.* 28(8):913-29.

Apolipoproteins utilized by the invention further include peptides that correspond to apolipoproteins as well as agonists that mimic the activity of ApoA-I, ApoA-I$_M$, ApoA-II, ApoA-IV, and ApoE, such as those disclosed in U.S. Pat. Nos. 6,004,925, 6,037,323 and 6,046,166 (issued to Dasseux et al.), and in U.S. Pat. No. 5,840,688 (issued Nov. 24, 1998 to Tso); and which are incorporated herein by reference in their entireties.

Such peptides can be synthesized or manufactured using any technique for peptide synthesis known in the art, see, e.g., the techniques described in U.S. Pat. Nos. 6,004,925, 6,037, 323 and 6,046,166. Stable preparations that have a long shelf life may be made by lyophilizing the peptides—either to prepare bulk for reformulation, or to prepare individual aliquots or dosage units that can be reconstituted by rehydration with sterile water or an appropriate sterile buffered solution prior to administration to a subject.

The Apo-SM complexes may include a single type of apolipoprotein, or mixtures of two or more different apolipoproteins, which may be derived from the same or different species. Although not required, the Apo-SM complexes will preferably comprise apolipoproteins derived from the animal species being treated, in order to avoid inducing an immune response to the therapy.

The apolipoprotein(s) may be complexed with many types of SM analogues or derivatives. In general, for a SM analogue or derivative to be effective in an Apo-SM complex of the invention, it can be impervious to hydrolysis by LCAT, as is naturally occurring SM. SM is a phospholipid very similar in structure to phosphatidylcholine, but with an amide bond instead of an ester bond. SM is not a substrate for LCAT and generally cannot be hydrolyzed by it. It can act, however, as an inhibitor of LCAT or can decrease LCAT activity by diluting the concentration of the substrate phospholipid. Because SM is not hydrolyzed, it remains longer in the circulation. This feature permits complexes comprising Apo-SM to have longer duration of pharmacological effect (mobilization of cholesterol) and to pick up more lipids, in particular cholesterol. This will results in less frequent or smaller doses necessary for treatment with Apo-SM particles.

The apolipoprotein(s) may be complexed with SM derived from virtually any source. For example, the SM may be obtained from milk, egg or brain. SM analogues or derivatives may also be used. Non-limiting examples of useful SM analogues and derivatives include, but are not limited to, palmitoylsphingomyelin and stearoylsphingomyelin.

The sphingomyelin may be artificially enriched in one particular saturated or unsaturated acyl chain. For example, milk sphingomyelin (Avanti Phospholipid, Alabaster, Ala.) is characterized by long saturated acyl chains. Milk sphingomyelin comprises about 20% of C16:0 (16 carbon, saturated) acyl chain compared to the 80% comprised in egg sphingomyelin. Using solvent extraction, milk sphingomyelin can be enriched in one particular acyl chain to have a composition in acyl chain comparable to, e.g., egg sphingomyelin. Acyl chains that may be utilized by the invention include, but are not limited to saturated acyl chains (such as dipalmitoyl, distearoyl, diarachidonyl, and dibenzoyl acyl chains), unsaturated chains (such as dioleoyl chains), mixed chains of saturated and unsaturated acyl chains (such as palmitoyl or oleoyl chains), saturated and/or unsaturated chains of mixed lengths, and ether analogues of saturated and unsaturated acyl chains.

The SM may be semi-synthetic such that it has a particular acyl chain. For example, milk sphingomyelin can be first purified from milk, then one particular acyl chain, e.g., the C16:0 acyl chain, can be cleaved and replaced by another acyl chain (preferably palmitic acid or oleic acid).

SM can also be entirely synthesized, by e.g., large-scale synthesis. See, e.g., Dong et al., U.S. Pat. No. 5,220,043, entitled Synthesis of D-erythro-sphingomyelins, issued Jun. 15, 1993; Weis, 1999, *Chem. Phys. Lipids* 102(1-2):3-12. Preferably, a predefined saturation level and fatty acid composition is selected for the synthetic SM.

The complexes may optionally also include one or more other phospholipids in addition to the SM. Virtually any type of phospholipid may be used, including, but not limited to, small alkyl chain phospholipids, phosphatidylcholine (PC), egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1-palmitoyl-2-oleoylphosphatidylcholine, 1-oleoyl-2-palmitylphosphatidylcholine, dioleoylphosphatidylcholine dioleoylphosphatidylethanolamine, dilauroylphosphatidylglycerol phosphatidylcholine, phosphatidylserine, phosphatidylethanolamine, phosphatidylinositol, sphingomyelin, sphingolipids, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipahmitoylphosphatidylserine, brain phosphatidylserine, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. The compositions will typically comprise about 40-85 wt % total phospholipid and about 60-15 wt % total apolipoprotein. (This range corresponds to roughly 1:25 to 1:200 molar ratio of apolipoprotein to phospholipid). If an optional second phospholipid is included, the sphingomyelin should typically comprise from about 25 to 75 wt % of the total phospholipid component, with the balance being the second type of phospholipid.

The apolipoprotein-phospholipid complexes can be complexed in phospholipid:apolipoprotein ratios (Ri) that vary depending on the apolipoprotein and the nature of the SM and other phospholipid(s) comprised in the complex, as well as the expected size of the complex ranging in size from 2-12 nm. For ApoA-I, the phospholipid:ApoA-I molar ratio may vary from 25 to 200. The percentage of SM in the complex may vary from 25% to 100% of the total phospholipid composition. For example, SM:PC:ApoA-I could be 25:25:1 (Ri=50) or 75:75:1 (Ri=150). Ratios in weight can be obtained by using a MW of 650-800 for the phospholipid.

The complexes may optionally also include paraoxonase (PON), antioxidants, cyclodextrins or other materials that help trap cholesterol in the core or the surface of the HDL-like particle. HDL particle may optionally be pegylated (e.g., covered with polyethylene glycol or other polymer) to increase circulation half-life.

Apolipoprotein, phospholipid, and Apo-phospholipid complexes utilized by the invention also include molecules that are labeled with any art-known detectable marker, including stable isotopes (e.g., $^{13}C$, $^{15}N$, $^{2}H$, etc.); radioactive isotopes (e.g., $^{14}C$, $^{3}H$, $^{125}I$, etc.); fluorophores; chemiluminescers; or enzymatic markers.

5.2. Methods of Making Apo-SM Complexes

Apo-SM complexes can be prepared in a variety of forms, including, but not limited to vesicles, liposomes, proteoliposomes, micelles, and discoidal particles. A variety of methods well known to those skilled in the art can be used to prepare the Apo-SM complexes. A number of available techniques for preparing liposomes or proteoliposomes may be used. For example, apolipoprotein can be co-sonicated (using a bath or probe sonicator) with the appropriate lipid (i.e., sphingomyelin) to form complexes. Alternatively, apolipoprotein can be combined with preformed lipid vesicles resulting in the spontaneous formation of Apo-SM complexes. The Apo-SM complexes can also be formed by a detergent dialysis method; e.g., a mixture of Apo, SM and a detergent such as cholate is dialyzed to remove the detergent and reconstituted to form Apo-SM complexes (see, e.g., Jonas et al., 1986, *Methods Enzymol*. 128:553-82), or by using an extruder device or by homogenization.

In one embodiment, Apo-SM complexes can be prepared by the cholate dispersion method as described in Section 6.1 (Example 1). Briefly, dry lipid is hydrated in $NaHCO_3$ buffer, then vortexed and sonicated until all lipid is dispersed. Cholate solution is added, the mixture is incubated for 30 minutes, with periodic vortexing and sonicating, until it turns clear, indicating that the lipid cholate micelles are formed. ProApoA-I in $NaHCO_3$ buffer is added, and the solution incubated for 1 hour at approximately 37° C.-50° C. The ratio of lipid:proApoA-I in the solution can be from 1:1 to 200:1 (mole/mole), but in a preferred embodiment, the ratio is 2:1 weight of lipid to weight of protein (wt/wt).

Cholate can be removed by methods well known in the art. For example cholate can be removed by dialysis, ultrafiltration or by removal of cholate molecules by adsorption absorption onto an affinity bead or resin. In one embodiment, the affinity beads, e.g., BIO-BEADS® (Bio-Rad Laboratories) are added to the preparation of Apo-lipid complexes and cholate to adsorb the cholate. In another embodiment, the preparation, e.g., a micellar preparation of the Apo-SM complexes and cholate, is passed over a column packed with affinity beads.

In a specific embodiment, cholate is removed from a preparation of proApoA-I-lipid complexes by loading the preparation onto BIO-BEADS® within a syringe. The syringe is then sealed with barrier film and incubated with rocking at 4° C. overnight. Before use, the cholate is remove by injecting the solution through BIO-BEADS®, where it is adsorbed by the beads.

The Apo-SM complexes have an increased half-life in the circulation when the complexes have a similar size and density to HDL, especially to the HDLs in the pre-β-1 or pre-β-2 HDL populations. Stable preparations having a long shelf life may be made by lyophilization—the co-lyophilization procedure described below being a preferred approach due to the stability of the resulting formulation and the ease of formulation/particle preparation process. Co-lyophilization methods are also described in U.S. Pat. No. 6,287,590 (entitled Peptide/lipid complex formation by co-lyophilization, by Dasseux, issued Sep. 11, 2001), which is incorporated herein by reference in its entirety. The lyophilized Apo-SM complexes can be used to prepare bulk for pharmaceutical reformulation, or to prepare individual aliquots or dosage units that can be reconstituted by rehydration with sterile water or an appropriate buffered solution prior to administration to a subject.

As disclosed above, apolipoprotein may be complexed with a variety of sphingomyelins. The sphingomyelin may be artificially enriched in one particular saturated or unsaturated acyl chain. For example, milk sphingomyelin (Avanti Phospholipid, Alabaster, Ala.) is characterized by long saturated acyl chains. Milk sphingomyelin comprises about 20% of C16:0 (16 carbon, saturated) acyl chain compared to the 80% comprised in egg sphingomyelin. Using solvent extraction, milk sphingomyelin can be enriched in one particular acyl chain to have a composition in acyl chain comparable to, e.g., egg sphingomyelin. Acyl chains that may be utilized by the invention include, but are not limited to, saturated acyl chains (such as dipalmitoyl, distearoyl, diarachidonyl, and dibehenoyl acyl chains), unsaturated chains (such as dioleoyl chains), mixed chains of saturated and unsaturated acyl chains (such as palmitoyl or oleyl chains), saturated and/or unsaturated chains of mixed lengths, and ether analogues of saturated and unsaturated acyl chains.

In certain preferred embodiments, a source of natural sphingomyelin is selected to avoid contamination by prions (e.g., in brain sphingomyelin) or viral contamination (e.g., in egg sphingomyelin). In another preferred embodiment, fully synthetic SM is selected to avoid contamination. In other embodiments, a SM with a high saturation state is used to improve chemical stability of the Apo-AI-SM complex.

The SM may be semi-synthetic such that it has a particular acyl chain. For example, milk sphingomyelin can be first purified from milk, then one particular acyl chain, e.g., the C16:0 acyl chain, can be cleaved and replaced by another acyl chain (preferably palmitic acid or oleic acid).

SM can also be entirely synthesized, by e.g., large-scale synthesis (see, e.g., Dong et al., U.S. Pat. No. 5,220,043, entitled Synthesis of D-erythro-sphingomyelins, issued Jun. 15, 1993; Weis, 1999, *Chem. Phys. Lipids* 102(1-2):3-12). Preferably, a predefined saturation level and fatty acid composition is selected for the synthetic SM.

U.S. Pat. Nos. 6,004,925, 6,037,323, 6,046,166 and 6,287,590 (incorporated herein by reference in their entireties) disclose a simple method for preparing apolipoprotein-lipid (Apo-lipid) complexes that have characteristics similar to HDL. This preferred method, co-lyophilization of Apo and lipid solutions in organic solvent (or solvent mixtures) and formation of Apo-lipid complexes during hydration of the lyophilized powder, has the following advantages: (1) The method requires very few steps. (2) The method uses inexpensive solvent(s). (3) Most or all of the included ingredients are used to form the designed complexes, thus avoiding waste of starting material that is common to the other methods. (4) Lyophilized compounds are formed that are very stable during storage. The resulting complexes may be reconstituted immediately before use. (5) The resulting complexes usually need not be further purified after formation and before use. (6) Toxic compounds, including detergents such as cholate, are avoided. (7) The production method can be easily scaled up and is suitable for GMP manufacture (i.e., in an endotoxin-free environment).

In a preferred embodiment, co-lyophilization methods commonly known in the art are used to prepare Apo-SM complexes. Briefly, the co-lyophilization steps include solubilizing Apo and lipid in organic solvent of solvent mixture, or solubilizing Apo and lipid separately and mixing them together. The desirable characteristics of solvent or solvent mixture are: (i) a medium relative polarity to be able to dissolve hydrophobic lipids and amphipatic protein, (ii) solvents should be class 2 or 3 solvent according to FDA solvent guidelines (Federal Register, volume 62, No. 247) to avoid potential toxicity associated with the residual organic solvent, (iii) low boiling point to assure ease of solvent removal during lyophilization, (iv) high melting point to provide for faster freezing, higher temperatures of condenser and, hence less ware of freeze-dryer. In a preferred embodiment, glacial acetic acid is used. Combinations of e.g., methanol, glacial acetic acid, xylene, or cyclohexane may also be used.

The Apo/Lipid solution is then lyophilized to obtain homogeneous Apo/lipid powder. The lyophilization conditions can be optimized to obtain fast evaporation of solvent with minimal amount of residual solvent in the lyophilized Apo/lipid powder. The selection of freeze-drying conditions can be determined by the skilled artisan, and depends on the nature or solvent, type and dimensions of the receptacle, e.g., vial, holding solution, fill volume, and characteristics of freeze-dryer used. The concentration of lipid/Apo solution prior to the lyophilization, for organic solvent removal and successful formation of complexes, is preferably 10 to 50 mg/ml concentration of Apo and 20 to 100 mg/ml concentrations of lipid.

The Apo-lipid complexes form spontaneously after hydration of Apo-lipid lyophilized powder with an aqueous media of appropriate pH and osmolality. In some embodiments, the media may also contain stabilizers such as sucrose, trehalose, glycerin and others. In some embodiments, the solution must be heated several times above transition temperature for lipids for complexes to form. The ratio of lipid to protein for successful formation of Apo-SM complexes can be from 1:1 to 200:1 (mole/mole), and is preferably 2:1 weight of lipid to weight of protein (wt/wt). Powder is hydrated to obtain final complex concentration of 5-30 mg/ml expressed in protein equivalents.

In one embodiment, Apo powder is obtained by freeze-drying Apo solution in $NH_4HCO_3$ aqueous solution. A homogeneous solution of Apo and lipid (i.e., sphingomyelin) is formed by dissolving their powders and Apo in glacial acetic acid. The solution is then lyophilized, and HDL-like Apo-lipid complexes are formed by hydration of lyophilized powder with aqueous media.

The another preferred method is homogenization. This method may be used to prepare Apo soybean-PC complexes and is routinely used for formulation of AI-$_{Milano}$-POPC complexes. Homogenization can be easily adapted for formation of Apo-SM complexes. Briefly, this method comprises forming a suspension of lipids in aqueous solution of Apo by Ultraturex™, and homogenization of formed lipid-protein suspension using high-pressure homogenizer until suspension becomes clear-opalescent solution and complexes are formed. Elevated temperatures above lipid transition are used during homogenization. Solution is homogenized for extended period of time 1-14 hours and elevated pressure.

In another embodiment, Apo-SM complexes are formed by co-lyophilization of phospholipid with peptide or protein solutions or suspensions. The homogeneous solution of peptide/protein and SM (plus any other phospholipid of choice) in an organic solvent or organic solvent mixture can be lyophilized, and Apo-SM complexes can be formed spontaneously by hydration of the lyophilized powder with an aqueous buffer. Examples of organic solvents or their mixtures are include, but are not limited to, acetic acid, acetic acid and xylene, acetic acid and cyclohexane, and methanol and xylene.

A suitable proportion of protein (peptide) to lipid can be determined empirically so that the resulting complexes possess the appropriate physical and chemical properties; i.e., usually (but not necessarily) similar in size to HDL. The resulting mixture of Apo and lipid in solvent is frozen and lyophilized to dryness. Sometimes an additional solvent must be added to the mixture to facilitate lyophilization. This lyophilized product can be stored for long periods and will remain stable.

The lyophilized product can be reconstituted in order to obtain a solution or suspension of the Apo-lipid complex. To this end, the lyophilized powder is rehydrated with an aqueous solution to a suitable volume (typically 5-20 mg Apo-SM complex/ml) which is convenient for e.g., intravenous injection. In a preferred embodiment the lyophilized powder is rehydrated with phosphate buffered saline, saline bicarbonate, or a physiological saline solution. The mixture may be agitated or vortexed to facilitate rehydration. In general, the reconstitution step should be conducted at a temperature equal to or greater than the phase transition temperature of the lipid component of the complexes. Within minutes of reconstitution, a clear preparation of reconstituted Apo-lipid complexes will result.

An aliquot of the resulting reconstituted preparation can be characterized to confirm that the complexes in the preparation have the desired size distribution; e.g., the size distribution of HDL. Characterization of the reconstituted preparation can be performed using any method known in the art, including, but not limited to, size exclusion filtration, gel filtration, column filtration, and gel permeation chromatography.

For example, after hydration of lyophilized Apo-lipid powder or at the end of homogenization or cholate dialysis formed Apo-lipid HDL-like particles are characterized with respect to their size, concentration, final pH and osmolality of resulting solution, in some instances integrities of lipid and apolipoprotein are characterized. The size of the resulting Apo-lipid particles is determinative of their efficacy, therefore making this measurement is preferred for characterization of the particles.

In one embodiment, gel permeation chromatography (GPC), e.g., a high pressure liquid chromatography system equipped with a 1×30 cm Superdex™ column (Pharmacia Biotech) and UV-detector may be used. Complexes are eluted with bicarbonate buffered saline comprised of 140 mM NaCl and 20 mM sodium bicarbonate delivered with 0.5 ml/min flow rate. A typical amount of complex injected is 0.1 to 1 mg based on protein weight. The complexes are monitored by absorbance at 280 nm.

Protein and lipid concentration of Apo-lipid particles solution can be measured by any method known in the art, including, but not limited to, protein and phospholipid assays as well as by chromatographic methods such as HPLC, gel filtration chromatography, GC coupled with various detectors including mass spectrometry, UV or diode-array, fluorescent, elastic light scattering and others. The integrity of lipid and proteins can be also determined by the same chromatographic techniques as well as peptide mapping, SDS-page gel, N- and C-terminal sequencing for proteins and standard assays to determine lipid oxidation for lipids.

5.3 Pharmaceutical Compositions

The pharmaceutical compositions utilized by the invention comprise Apo-SM complexes as the active ingredient in a pharmaceutically acceptable carrier suitable for administration and delivery in vivo. Since peptides may comprise acidic and/or basic termini and/or side chains, peptides can be included in the compositions in either the form of free acids or bases, or in the form of pharmaceutically acceptable salts.

Injectable compositions include sterile suspensions, solutions or emulsions of the active ingredient in aqueous or oily vehicles. The compositions can also comprise formulating agents, such as suspending, stabilizing and/or dispersing agent. The compositions for injection can be presented in unit dosage form, e.g., in ampules or in multidose containers, and can comprise added preservatives. For infusion, a compositions is preferably supplied in an infusion bag made of material compatible with Apo-lipid complexes, such as ethylene vinyl acetate or any other compatible material known in the art.

Alternatively, the injectable compositions can be provided in powder form for reconstitution with a suitable vehicle, including but not limited to, sterile pyrogen free water, buffer, dextrose solution, etc., before use. To this end, Apo can be lyophilized, or co-lyophilized Apo-SM complexes may be prepared. The stored compositions can be supplied in unit dosage forms and reconstituted prior to use in vivo.

For prolonged delivery, the active ingredient can be formulated as a depot composition, for administration by implantation; e.g., subcutaneous, intradermal, or intramuscular injection. Thus, for example, Apo-lipid complex or Apolipoprotein alone may be formulated with suitable polymeric or hydrophobic materials (e.g., as an emulsion in an acceptable oil) or in phospholipid foam or ion exchange resins.

Alternatively, transdermal delivery systems manufactured as an adhesive disc or patch that slowly releases the active ingredient for percutaneous absorption can be used. To this end, permeation enhancers can be used to facilitate transdermal penetration of the active ingredient. A particular benefit can be achieved by incorporating the Apo-SM complexes utilized by the invention into a nitroglycerin patch for use in patients with ischemic heart disease and hypercholesterolemia.

The compositions can, if desired, be presented in a pack or dispenser device that may comprise one or more unit dosage forms comprising the active ingredient. The pack can for example comprise metal or plastic foil, such as a blister pack. The pack or dispenser device can be accompanied by instructions for administration.

5.4 Methods of Treatment

The Apo-SM complexes utilized by the invention can be used to treat or prevent virtually any disease, condition or disorder responsive to apolipoproteins or other apolipoprotein-phospholipid particles (e.g., ApoAI-SoybeanPC, ApoAI-POPC), including but not limited to, coronary heart disease; coronary artery disease; cardiovascular disease, hypertension, restenosis, vascular or perivascular diseases; dyslipidemic disorders; dyslipoproteinemia; high levels of low density lipoprotein cholesterol; high levels of very low density lipoprotein cholesterol; low levels of high density lipoproteins; high levels of lipoprotein Lp(a) cholesterol; high levels of apolipoprotein B; atherosclerosis (including treatment and prevention of atherosclerosis); hyperlipidemia; hypercholesterolemia; familial hypercholesterolemia (FH); familial combined hyperlipidemia (FCH); lipoprotein lipase deficiencies, such as hypertriglyceridemia, hypoalphalipoproteinemia, and hypercholesterolemialipoprotein.

Using the methods of the invention, a dosage of apolipoprotein from 2- to 25-fold less than the effective dosage currently known in the art would be expected to be efficacious in treating or preventing the disease or in bringing about an ameliorative effect.

In one embodiment, the methods of the invention encompass a method of treating or preventing a disease associated with dyslipidemia, comprising administering to a subject a composition comprising an apolipoprotein and sphingomyelin in an amount effective to achieve a serum level of free or complexed apolipoprotein in the range of 10 mg/dL to 300 mg/dL above a baseline (initial) level before administration between 5 minutes and 1 day after administration.

In another embodiment, the methods of the invention encompass a method of treating or preventing a disease associated with dyslipidemia, comprising administering to a subject an apolipoprotein-sphingomyelin complex in an amount effective to achieve a circulating plasma concentrations of a HDL-cholesterol fraction between 10% and 1000% of the initial HDL-cholesterol fraction concentration between 5 minutes and 1 day after administration.

In another embodiment, the methods of the invention encompass a method of treating or preventing a disease associated with dyslipidemia, comprising administering to a subject an apolipoprotein-sphingomyelin complex in an amount effective to achieve a circulating plasma concentration of a HDL-cholesterol fraction between 30 and 300 mg/dL between 5 minutes and 1 day after administration.

In another embodiment, the methods of the invention encompass a method of treating or preventing a disease associated with dyslipidemia, comprising administering to a subject an apolipoprotein-sphingomyelin complex in an amount effective to achieve a circulating plasma concentrations of cholesteryl esters between 30 and 300 mg/dL between 5 minutes and 1 day after administration.

The Apo-SM complexes can be used alone or in combination therapy with other drugs used to treat or prevent the foregoing conditions. Such therapies include, but are not limited to simultaneous or sequential administration of the drugs involved. For example, in the treatment of hypercholesterolemia or atherosclerosis, the Apo-SM formulations can be administered with any one or more of the cholesterol lowering therapies currently in use; e.g., bile-acid resins, niacin, statins and/or fibrates. Such a combined regimen may produce particularly beneficial therapeutic effects since each drug acts on a different target in cholesterol synthesis and transport; i.e., bile-acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the Apo-SM complexes affect RCT, increase HDL, and promote cholesterol efflux.

In another embodiment, the Apo-SM complexes may be used in conjunction with fibrates to treat or prevent coronary heart disease; coronary artery disease; cardiovascular disease, hypertension, restenosis, vascular or perivascular diseases; dyslipidemic disorders; dyslipoproteinemia; high levels of low density lipoprotein cholesterol; high levels of very low density lipoprotein cholesterol; low levels of high density lipoproteins; high levels of lipoprotein Lp(a) cholesterol; high levels of apolipoprotein B; atherosclerosis (including treatment and prevention of atherosclerosis); hyperlipidemia; hypercholesterolemia; familial hypercholesterolemia (FH); familial combined hyperlipidemia (FCH); lipoprotein lipase deficiencies, such as hypertriglyceridemia, hypoalphalipoproteinemia, and hypercholesterolemialipoprotein. Exemplary formulations and treatment regimens are described below.

The Apo-SM complexes utilized by the invention may be administered by any suitable route that ensures bioavailability in the circulation. An important feature of the invention is that Apo-SM complexes may be administered in doses less than 1-10% of the effective dose required for apolipoprotein (Apo) or Apo peptide administered alone, and in doses 2-25 fold less than the effective dose required for Apo-soybean PC (or Apo-egg PC or Apo-POPC) administration. Administration at doses (for intravenous injection) as low as about 40 mg to 2 g/person of apolipoprotein every 2 to 10 days is required, rather than the large amounts of apolipoprotein (20 mg/kg to 100 mg/kg per administration every 2 to 5 days, 1.4 g to 8 g per average sized human) required by currently available treatment regimens.

The Apo-SM complexes utilized by the invention are administered in dosages that increase the small HDL fraction, and preferably, the pre β- (and pre-γ), and pre-β-like HDL fraction.

Administration can best be achieved by parenteral routes of administration, including intravenous (IV), intramuscular (IM), intradermal, subcutaneous (SC), and intraperitoneal (IP) injections. In certain embodiments, administration is by a perfuser, an infiltrator or a catheter. In a preferred embodiments, the Apo-SM complexes are administered by injection, by a subcutaneously implantable pump or by a depot preparation, in amounts that achieve a circulating serum concentration equal to that obtained through parenteral administration.

Administration can be achieved through a variety of different treatment regimens. For example, several intravenous injections can be administered periodically during a single day, with the cumulative total volume of the injections not reaching the daily toxic dose. Alternatively, one intravenous injection can be administered about every 3 to 15 days, preferably about every 5 to 10 days, and most preferably about every 10 days. In yet another alternative, an escalating dose can be administered, starting with about 1 to 5 doses at a dose between (50-200 mg) per administration, then followed by repeated doses of between 200 mg and 1 g per administration. Depending on the needs of the patient, administration can be by slow infusion with a duration of more than one hour, by rapid infusion of one hour or less, or by a single bolus injection.

Complexing apolipoprotein with SM rather than with another lipid, e.g., phosphatidyl choline (PC), increases its toxicity at a given individual dose, because the complex removes more cholesterol from serum circulation, allowing it to have greater pharmacological efficacy and toxic effects. For example, if apolipoprotein-SM is parenterally administered, e.g., by injection, then it is toxic at a dose of 200 mg/kg. However, if injections are given at a lower dosage for several days, then gradually increased, the recipient will adapt to the administration and a higher final dosage can be achieved. For example, an injection can be administered on two sequential days at a concentration of 10 mg/kg, followed by injection on the next two sequential days at a concentration of 20 mg/kg, followed by injection on the next two sequential days at a concentration of 30 mg/kg followed by injection on subsequent days of 40 mg/kg per day. Under such a schedule, apolipoprotein-SM complexes can be administered for up to two weeks without problems of toxicity.

Other routes of administration may be used. For example, absorption through the gastrointestinal tract can be accomplished by oral routes of administration (including but not limited to ingestion, buccal and sublingual routes) provided appropriate formulations (e.g., enteric coatings) are used to avoid or minimize degradation of the active ingredient, e.g., in the harsh environments of the oral mucosa, stomach and/or small intestine. Alternatively, administration via mucosal tissue such as vaginal and rectal modes of administration may be utilized to avoid or minimize degradation in the gastrointestinal tract. In yet another alternative, the formulations of the invention can be administered transcutaneously (e.g., transdermally), or by inhalation. It will be appreciated that the preferred route may vary with the condition, age and compliance of the recipient.

The actual dose of Apo-SM complexes will vary with the route of administration. In one embodiment, the dose is adjusted to achieve a serum level of free or complexed apolipoprotein in the range of 10 mg/dl to 300 mg/dl above a baseline (initial) level before administration between 5 minutes and 1 day after administration. The baseline level is the initial apolipoprotein level prior to administration of the Apo-SM complexes.

In another embodiment, the dose is adjusted to achieve a circulating plasma concentrations of a HDL-cholesterol fraction between 10% and 1000% of the initial HDL-cholesterol fraction concentration between 5 minutes and 1 day after intravenous administration.

In another embodiment, the dose is adjusted to achieve a temporary or permanent circulating plasma concentrations of a HDL-cholesterol fraction between 30 and 300 mg/dl between 5 minutes and 1 day after intravenous administration.

In another embodiment, the dose is adjusted to achieve a temporary or permanent circulating plasma concentrations of cholesteryl esters between 30 and 300 mg/dl between 5 minutes and 1 day after intravenous administration.

Data obtained in animal model systems described in U.S. Pat. Nos. 6,004,925, 6,037,323 and 6,046,166 (issued to Dasseux et al., incorporated herein by reference in their entireties) show that ApoA-I peptides associate with the HDL component, and have a projected half-life in humans of about five days. Thus, in one embodiment, Apo-SM complexes can be administered by intravenous injection at a dose between about 0.1 g-1 g of Apo-SM per administration every 2 to 10 days per average sized human.

Toxicity and therapeutic efficacy of the various Apo-SM complexes can be determined using standard pharmaceutical procedures in cell culture or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Apo-SM complexes that exhibit large therapeutic indices are preferred.

Patients can be treated from a few days to several weeks before a medical act (e.g., preventive treatment), or during or after a medical act. Administration can be concomitant to or contemporaneous with another invasive therapy, such as, angioplasty, carotid ablation, rotoblader or organ transplant (e.g., heart, kidney, liver, etc.).

In certain embodiments, Apo-SM complexes are administered to a patient whose cholesterol synthesis is controlled by a statin or a cholesterol synthesis inhibitor. In other embodiments, Apo-SM complexes are administered to a patient undergoing treatment with a binding resin, e.g., a semi-synthetic resin such as cholestyramine, or with a fiber, e.g., plant fiber, to trap bile salts and cholesterol, to increase bile acid excretion and lower blood cholesterol concentrations.

5.5 Other Uses

The Apo-SM complexes utilized by the invention can be used in assays in vitro to measure serum HDL, e.g., for diagnostic purposes. Because ApoA-I, ApoA-II and Apo peptides associate with the HDL component of serum, Apo-SM complexes can be used as "markers" for the HDL population, and the pre-β1 and pre-β2 HDL populations. Moreover, the Apo-SM complexes can be used as markers for the subpopulation of HDL that are effective in RCT. To this end, the Apo-SM can be added to or mixed with a patient serum sample; after an appropriate incubation time, the HDL component can be assayed by detecting the incorporated Apo-SM. This can be accomplished using labeled Apo-SM (e.g., radiolabels, fluorescent labels, enzyme labels, dyes, etc.), or by immunoassays using antibodies (or antibody fragments) specific for Apo-SM.

Alternatively, labeled Apo-SM can be used in imaging procedures (e.g., CAT scans, MRI scans) to visualize the circulatory system, or to monitor RCT, or to visualize accumulation of HDL at fatty streaks, atherosclerotic lesions, and the like, where the HDL should be active in cholesterol efflux.

6. EXAMPLES 6.1. Example 1

Preparation of ProApoA-I-Lipid Complexes

Complexes of proApoA-I and phospholipids are drug candidates that potentially mimic the biological activities of HDL. This example describes the preparation of proApoA-I-phospholipid complexes.

6.1.1. Materials and Methods

Complexes of proApoA-I and lipids were prepared by the cholate dispersion method. Four lipids were used: Phospholipon 90 G (soybean PC), sphingomyelin, dipalmitoyl phosphatidylcholine (DPPC), and 1-palmitoyl-2-oleyl-phosphatidylcholine (POPC).

A 30 mg/ml cholate solution was made by adding 0.9677 g of cholic acid to 32.25 ml of 2 mM $NaHCO_3$ buffer.

To prepare the proApoA-I solution, proApoA-I solution (Eurogentec) at a concentration of 1 mg/ml in 6M urea was employed. 60 ml of the proApoA-I-6M urea solution was dialyzed against 1200 ml of 2 mM $NaHCO_3$ buffer using a tangential flow filtration unit (Labscale TFF System, Millipore) equipped with a 10 kDa cut off membrane. Following dialysis, the solution was concentrated to a final volume of 20 ml. Remaining solution was collected and the protein concentration was determined to be 2.62 mg/ml solution by a Markwell-Lowry protein assay (Markwell et al., 1978, *Anal. Biochem.* 87(1): 206-10).

To prepare the Phospholipon 90 G (soybean PC) solution, Phospholipon 90 G (Rhône-Poulenc Nattermann Phospholipid GMBH # 228154) was aliquoted into 50 ml aliquots and stored under $N_2$ gas at −20° C. A 25 mg/ml Phospholipon 90 G solution was made by adding 0.7815 g of Phospholipon 90 G to 31.26 ml of chloroform.

A 25 mg/ml sphingomyelin solution was made by adding 0.0637 g of sphingomyelin to 2.548 ml of chloroform.

25 mg/ml solutions of 1,2-Dipalmitoyl-sn-glycero-3-phosphocholine (DPPC) and 1-palmitoyl-2-oleyl-phosphatidylcholine (POPC) in chloroform were also prepared.

250 µl aliquots of the Phospholipon 90 G, sphingomyelin, DPPC and POPC solutions were then placed in glass tubes and the chloroform evaporated by $N_2$ blowing and vortexing to produce 6.25 mg of dry lipid per tube. 400 µl of 2 mM $NaHCO_3$ buffer was added to each tube and the lipids were hydrated for 15 min at 37° C., for all the lipids except DPPC, which was hydrated at 50° C. for 15 min. The tubes of solution were vortexed and sonicated periodically until all lipids were dispersed. 160 µl of the 30 mg/ml cholate solution was added to each tube.

160 ml of the 30 mg/ml cholate solution was added to each tube to clarify the sphingomyelin solution. The lipid-cholate solutions were incubated at 37° C. (for POPC, SM, and soybean PC) and 50° C. (for DPPC). During incubation, solutions were periodically vortexed and sonicated. If solutions would not clear after vortexing and sonicating steps, then additional cholate solution was added to the lipid-cholate solution in a series of 100 ml aliquots. Incubation, vortex, sonication and addition of cholate continued until all solutions became clear. Total cholate solution added was 160, 260, 560 and 560 ml for the SM, DPPC, soybean PC, and POPC, respectively. The lipid-cholate solutions were incubated for a total of 30 min.

1.908 ml of the 2.62 mg/ml solution of proApoA-I in 2 mM $NaHCO_3$ buffer was added to each tube. The ratio of proApoA-I:lipid in the solution was 5 mg:6.25 mg or 1:1.25 (wt/wt). The proApoA-I-lipid-cholate solutions were incubated for 1 h at 37° C. (for POPC, SM, and soybean PC) and at 50° C. (for DPPC).

To remove cholate, which is toxic, the solutions were incubated with ion exchange resin (BIO-BEADS®, Sigma). BIO-BEADS® were activated by incubation of one volume of dry BIO-BEADS® with two volumes of 2 mM $NaHCO_3$ for 6 hours. Ten ml and 30 ml plastic syringes were loaded with activated BIO-BEADS®. The preparation of proApoA-I-lipid complexes was then loaded onto the BIO-BEADS®. For the sphingomyelin and DPPC solutions, approximately 5-7 ml of BIO-BEADS® were added per 4.8 mg of cholate solution. For soybean PC and POPC, approximately 12 ml of BIO-BEADS® were added per 16.8 mg of cholate solution. The proApoA-I-lipid complex solutions were then loaded on the BIO-BEADS® within the syringes. The syringes were then sealed with barrier film and incubated with rocking at 4° C. overnight. At the end of incubation, solutions of the proApo-A-I-lipid complexes were collected and filtered through 0.22 mm PES filters. Solutions were then stored at 4° C. prior to the analysis.

Complex solutions were analyzed using GPC (gel permeation chromatography) using a 1×30 cm Superdex™ 200 (Pharmacia Biotech) column. An aqueous mobile phase containing 20 mM $NaHCO_3$ (pH 8) was delivered at a 0.5 ml/min flow rate. The injection volume was 100 μl. The run time was 45 min. Complex was detected by absorption at 280 nm. The retention time of the proApoA-I-lipid complex was compared with the retention time of purified rabbit HDL.

6.1.2. Results and Discussion

Chromatograms of proApo-A-I complexes contained two major peaks: the first, appearing at around 22 min, corresponded to a molecular weight of roughly 200-300 kDa. The second, appearing at around 26 min, corresponded to a molecular weight of roughly 100 kDa. In each chromatogram, the peak at 22 min corresponded to lipid-rich proApo-A-I lipid complexes, while the peak at 26 min corresponded to lipid poor proApo-A-I lipid complexes. The chromatogram of purified rabbit HDL standard produced a single peak at around 20 min. Calculated from the retention time of the purified rabbit HDL, the formulation was optimized to yield a monomodal peak at around 22 min of lipid-rich proApo-AI complexes.

The ratio between the 22 min and 26 min peaks was differed for different lipids. For proApo-A-I-POPC and proApo-A-I-soybean PC complexes at a ratio of 1:1.25 protein/lipid (wt/wt), the fraction of 26 min peak area, in relation to the total area, was only 10-20%. Therefore, no further optimization was required for these complexes. In contrast, for proApo-A-I-SM and proApo-A-I DPPC complexes at 1:1.25 (wt/wt) protein/lipid ratio, the fraction of 26 min peak area in relation to the total area was 30-50%. The difference between 22 min and 26 min peak ratio for the different lipids could be attributed the variations in molecular weight and structure of the lipids, and, therefore, different wt/wt ratios of protein to lipid required to form lipid-rich complexes. In order to increase the fraction of lipid-rich, 22 min peak for proApo-A-I SM complexes, the wt/wt ratio of SM to protein was increased in Example 2 below.

6.2. Example 2

Further Preparation of ProApoA-I-Lipid Complexes

Based on the results obtained in Section 6.1 (Example 1), the proportion of SM was increased, in order to produce preferentially a single peak of proApoA-I-SM complexes. This example demonstrates that the proApoA-I to sphingomyelin ratio may be varied to produce a single peak of proApoA-I-sphingomyelin complex at a ratio of 1:2 (wt/wt).

6.2.1. Materials and Methods

ProApoA-I-SM complexes were prepared by the following co-solubilization method.

ProApoA-I solution in 6M urea (Eurogentec) was concentrated 5 times and dialyzed against 10 volumes of 5 mM $NH_4HCO_3$. The protein concentration was then measured by performing a Markwell-Lowry protein assay. Protein solution was then lyophilized.

A 25 mg/ml stock solution of proApoA-I in acetic acid was made by dissolving 128.2 mg of the lyophilized proApo-A-I powder in 5.13 ml of glacial acetic acid (JT Baker).

A 50 mg/ml stock solution of sphingomyelin was made by dissolving 256.0 mg of sphingomyelin (Avanti) in 5.12 ml of glacial acetic acid.

Solutions of proApoA-I:SM were combined to weight: weight (wt/wt) ratios of 1:1, 1:1.25, 1:1.5 and 1:2 by combining 1.0 ml of proApo-A-I stock solution with 0.5, 0.625, 0.75 and 1.0 ml of sphingomyelin stock solution. The combined solutions were filtered using a syringe-driven 0.2 μm polyethersulfone filter (Whatman) and the volume of filtered solution was recorded.

Solutions of proApoA-I-SM were frozen at −40° C. for approximately 1.5 hours, then lyophilized in a freeze-dryer as indicated at the temperatures and in the order shown below:

| Temperature | Time |
| --- | --- |
| −20° C. | 2 h |
| −20° C. to 23° C. | 12 h |
| 50° C. | 6 h |
| 23° C. | 1.5 h |

ProApoA-I SM complexes were formed by hydrating the lyophilized powder in bicarbonate saline (140 mM NaCl, 20 mM $NaHCO_3$) to a concentration of 10 mg/ml protein. Solutions were heated to 52° C. and cooled to room temperature three times in order to facilitate hydration.

Aliquots of 200 μl of complex solutions were diluted using 200 μl bicarbonate saline and analyzed on a Superdex 200 HR 10/30 GPC column (Amersham Pharmacia Biotech AB) using the following conditions. Running buffer was 140 mM NaCl and 20 mM $NaHCO_3$. The flow rate was 0.5 ml/min. The run time was 50 min. The injection volume was 10 μl. Detection wavelength was 220 nm. The retention times of complexes was compared to the retention time of a gel filtration standard (Bio-Rad).

6.2.2. Results and Discussion

Chromatograms contained two major peaks at 24 and 29 min. The peak at 24 min corresponded to proApoA-I-SM complexes while the peak at 29 min corresponded to free proApoA-I protein. The ratio between the 24 and 29 min peaks differed depending upon the ratio of proApo-A-I-SM with a greater percentage of the peak appearing in the complex portion as the wt/wt ratio increased. At 1:2 wt/wt of proApoA-I:SM, a single peak at 24 min was observed, hence, homogeneous distribution of complex size was obtained.

6.3. EXAMPLE 3

Pharmacological Efficacy of
R-ProApoA-I-Sphingomyelin Complexes Compared
with R-ProApoA-I-POPC Complexes ProApoA-I-lipid complexes are drug candidates that potentially mimic the biological activities of HDL. The objective of this study was to compare the pharmacodynamic properties (i.e., mobilization of cholesterol in plasma) of proApoA-I-SM with those of conventional proApoA-I-phosphotidyl choline complexes such as proApoA-I-POPC. Recombinant human proApoA-I (r-proApoA-I) was used in this study. Proapolipoprotein A-I comprises six amino acids (Arg-His-Phe-Trp-Gln-Glu; SEQ ID NO:1) attached at the amino terminal end of ApoA-I.

6.3.1. Materials and Methods

Complex Formulation

ProApoA-I-SM and proApoA-I-POPC complexes were prepared by the cholate dialysis method as described above. The ratio of apolipoprotein to lipid was 1:2 (weight of protein/weight of lipid) for proApoA-I-SM and proApo-A-I-POPC. The protein r-proApoA-I (Eurogentec, Belgium) solution in 1 mg/ml in 6M urea was dialyzed with 20 volumes of 5 mM $NH_4HCO_3$ solution (pH 8). Protein concentration after dialysis was determined by a Modified Lowry Assay.

Sodium cholate (Sigma) was added to the protein solution at a 1:2 ratio (weight of r-proApoA-I/weight of sodium cholate). Then phospholipids were added to the protein-cholate solutions at a 1:2 weight ratio of apolipoprotein to phospholipid. Protein-cholate-phospholipid solutions were incubated at 37° C. for solutions containing POPC and 50° C. for solutions containing SM. During incubation solutions were periodically mixed by vortexing.

After 1 hour of incubation, clear solutions were formed. Cholate, which is toxic for human and animals, was removed from solutions by incubation in presence of an ion exchange resin Biobeads™ (BioRad). Biobeads™ were added to protein-phospholipid-cholate solution at 1:2 ratio of hydrated Biobeads™ volume to solution volume. The resulting solutions were incubated for 12 hours at 4° C. under rocking. During the incubation, cholate was absorbed by Biobeads™ ion exchange resin. Removal of cholate resulted in formation of cholate free apolipoprotein-phospholipid complexes. At the end of incubation solutions were filtered to remove Biobeads™ and the resulting solutions were sterilized. Trehalose was added to the final solution at 80 mg/ml to adjust osmolality. The resulting solutions were analyzed and stored at 4° C. prior to injection into the animals.

Complex Characterization

After formulation, apolipoprotein-phospholipid complexes were analyzed to determine their size, protein concentration, solution pH and osmolality. Complex sizes were analyzed using GPC (gel permeation chromatography) equipped with a 1×30 cm Superdex™ 200 (Pharmacia Biotech) column. An aqueous mobile phase containing 20 mM $NaHCO_3$ (pH 8) was delivered at a 0.5 ml/min flow rate. The injection volume was 100 μl. Complexes were detected by UV absorption at 280 nm. Protein concentration was determined by routine methods (i.e., a modified Markwell Lowry assay).

Animal Studies Design

Random-bred, NZW female rabbits weighing approximately 3-3.6 kg were used in this study. The apolipoprotein-phospholipid complexes were injected intravenously by slow bolus infusion into the marginal ear vein. For blood sampling, approximately 1-2 ml of blood was collected from the lateral car vein in the non-injection ear (or in some cases, from the medial artery) using a 3 ml syringe without anticoagulant. All tubes collected without anticoagulant were kept at room temperature for 30-60 min for clotting. Blood samples were centrifuged within 1 hour after collection and the serum from each sample was separated into aliquots and stored a −80° C. until time of analysis.

Three rabbits received r-proApoA-I-POPC complexes while the other three received r-proApoA-I-SM complexes. Complexes were administered at 15 mg/kg dose based on the protein content. Blood samples were collected at pre-bleed, 5 min, 30 min, 1 h, 2 h, 24 h, and 48 h.

Analysis of Blood Samples

Serum phospholipid (Phospholipid B, Kit # 990-54009, Wako Chemicals GmbH, Neuss, Germany), triglycerides (Triglycerides, Kit # 1488872, Boehringer Mannheim Corporation, Indianapolis, Ind.), total cholesterol and unesterified cholesterol were determined with commercially available kits for a Hitachi 912 Automatic Analyzer (Roche Diagnostics Corporation, Indianapolis, Ind.).

Lipoprotein profiles were analyzed using gel filtration chromatography on a Superose 6HR 1×30 cm column equipped with on-line detection for total or free cholesterol as described by Kieft et al. (J Lipid Res 1991; 32:859-866, 1991). Esterified cholesterol in serum and in the lipoprotein fractions VLDL, LDL and HDL was calculated by subtracting free cholesterol from total cholesterol values.

Data Analysis

The time courses of absolute and percent changes in serum free (unesterified) cholesterol, HDL free (unesterified) cholesterol were plotted. Area under the curve for mobilized cholesterol were calculated by a trapezoidal method and compared for various r-pro-ApoA-I-phospholipid complexes.

6.3.2. Results and Discussion

ProApoA-I-SM and proApoA-I-POPC complexes (1:2 ratio of protein weight/phospholipid weight) were administered at 15 mg/kg dose (based on protein content) to NZW female rabbits. Unexpectedly, a significantly higher mobilization of free cholesterol was observed with administration of proApo-I-SM complexes compared to proApo-I-POPC complexes. The HDL free cholesterol increased by 31 mg/dl after 30 min following administration of proApoA-I-SM versus by 7 mg/dl 30 min following administration of proApoA-I-POPC complexes (FIG. 1).

In addition, large differences were observed in areas under the curves of free cholesterol and HDL free cholesterol concentration versus time for 0 to 24 h ($AUC_{0-24h}$) time period.

For HDL free cholesterol AUC0-24h values were 22.3 mg*hr/dl and 354.2 mg*hr/dl for r-proApoA-I-POPC and r-proApoA-I-SM complexes respectively. This indicates that r-proApoA-I-SM complexes mobilized 16 times more HDL-free cholesterol in 24 hours compared to r-proApoA-I-POPC complexes.

All cited references are incorporated herein by reference in their entirety and for all purposes to the same extent as if each individual publication, patent or patent application was specifically and individually indicated to be incorporated herein by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described are offered by way of example only, and the invention is to be limited only by the terms of the appended claims along with the full scope of equivalents to which such claims are entitled.

What is claimed is:

1. A method treating dyslipidemia or a disease associated with dyslipidemia in a subject comprising administering to a subject in need of treatment a complex comprising an apolipoprotein and the lipid 1-palmitoyl-2-oleoyl phosphatidylcholine (POPC), and determining the level of free HDL cholesterol in the serum of the subject, wherein the complex is administered in an amount sufficient to increase the free HDL cholesterol in the serum of the subject by about 7 mg/dL after administration.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: Synthetic Peptide

<400> SEQUENCE: 1

Arg His Phe Trp Gln Glu
1               5